(12) United States Patent
Franke et al.

(10) Patent No.: US 10,639,477 B2
(45) Date of Patent: *May 5, 2020

(54) SYSTEMS AND METHODS FOR DELIVERING PULMONARY THERAPY

(71) Applicant: Cardiac Pacemakers, Inc., St. Paul, MN (US)

(72) Inventors: Manfred Franke, Weissenborn Sa. (DE); Bryan Allen Clark, Forest Lake, MN (US); Aiden Flanagan, Kilcolgan (IE); Juan Gabriel Hincapie Ordonez, Maple Grove, MN (US); David J. Ternes, Roseville, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 301 days.

This patent is subject to a terminal disclaimer.

(21) Appl. No.: 14/597,131

(22) Filed: Jan. 14, 2015

(65) Prior Publication Data

US 2015/0202437 A1 Jul. 23, 2015

Related U.S. Application Data

(60) Provisional application No. 61/928,714, filed on Jan. 17, 2014.

(51) Int. Cl.
*A61N 1/36* (2006.01)
*A61N 1/05* (2006.01)
(Continued)

(52) U.S. Cl.
CPC ........ *A61N 1/3611* (2013.01); *A61B 18/1206* (2013.01); *A61N 1/0551* (2013.01);
(Continued)

(58) Field of Classification Search
CPC .. A61N 1/0519; A61N 1/0551; A61N 1/0556; A61N 1/0558; A61N 1/3601;
(Continued)

(56) References Cited

U.S. PATENT DOCUMENTS

| 4,608,985 A | 9/1986 | Crish et al. |
| 5,421,817 A | 6/1995 | Liss et al. |

(Continued)

FOREIGN PATENT DOCUMENTS

| AU | 2015206540 B2 | 8/2017 |
| AU | 2015206541 B2 | 12/2017 |

(Continued)

OTHER PUBLICATIONS

Franke, Manfred. "Translating Electric KHFAC and DC Nerve Block from Research to Application". PhD Thesis, Case Western Reserve University. May 2014.*

(Continued)

*Primary Examiner* — Eugene T Wu
(74) *Attorney, Agent, or Firm* — Schwegman Lundberg & Woessner, P.A.

(57) ABSTRACT

An example of a system may include an electrode and a pulse generation system. The electrode may be configured to be implanted near a neural target that innervates airways. The pulse generation system may be configured to be operably connected to the electrode to deliver depletion block stimulation through the electrode to alleviate symptoms of pulmonary disease. The pulse generation system and the electrode may be configured to cooperate to capture axons in the neural target. The depletion block stimulation may include a series of pulses at a depletion pulse frequency.

13 Claims, 21 Drawing Sheets

(51) Int. Cl.
*A61B 18/12* (2006.01)
*A61N 1/372* (2006.01)
*A61N 1/378* (2006.01)
*A61B 18/14* (2006.01)
*A61B 18/20* (2006.01)
*A61B 18/00* (2006.01)

(52) U.S. Cl.
CPC ....... *A61N 1/0558* (2013.01); *A61N 1/36053* (2013.01); *A61N 1/36067* (2013.01); *A61N 1/36071* (2013.01); *A61N 1/36117* (2013.01); *A61N 1/36128* (2013.01); *A61N 1/36171* (2013.01); *A61B 18/1477* (2013.01); *A61B 18/20* (2013.01); *A61B 2018/00577* (2013.01); *A61B 2018/00595* (2013.01); *A61N 1/36132* (2013.01); *A61N 1/36135* (2013.01); *A61N 1/3787* (2013.01); *A61N 1/37205* (2013.01); *A61N 1/37288* (2013.01)

(58) Field of Classification Search
CPC .............. A61N 1/36053; A61N 1/3611; A61N 1/36171; A61N 1/36146; A61N 1/3615; A61N 1/36153; A61N 1/36157; A61B 5/08; A61B 5/0809; A61B 5/085; A61B 5/6862
See application file for complete search history.

(56) References Cited

U.S. PATENT DOCUMENTS

| | | | |
|---|---|---|---|
| 7,389,145 B2 | 6/2008 | Kilgore et al. | |
| 7,734,355 B2 | 6/2010 | Cohen et al. | |
| 7,826,899 B1 | 11/2010 | Ryu et al. | |
| 7,949,399 B2 | 5/2011 | Wenzel et al. | |
| 8,060,208 B2 | 11/2011 | Kilgore et al. | |
| 8,229,564 B2 | 7/2012 | Rezai et al. | |
| 8,483,831 B1* | 7/2013 | Hlavka | A61B 18/08 600/529 |
| 9,242,097 B2 | 1/2016 | Mokelke et al. | |
| 10,201,709 B2 | 2/2019 | Franke et al. | |
| 10,413,731 B2 | 9/2019 | Franke et al. | |
| 2002/0055779 A1* | 5/2002 | Andrews | A61N 1/36014 623/11.11 |
| 2003/0233137 A1 | 12/2003 | Paul, Jr. | |
| 2004/0093093 A1 | 5/2004 | Andrews | |
| 2004/0111126 A1 | 6/2004 | Tanagho et al. | |
| 2004/0127953 A1* | 7/2004 | Kilgore | A61N 1/36071 607/46 |
| 2005/0021092 A1 | 1/2005 | Yun et al. | |
| 2005/0137644 A1 | 6/2005 | Boveja et al. | |
| 2005/0149148 A1 | 7/2005 | King | |
| 2005/0216070 A1* | 9/2005 | Boveja | A61N 1/08 607/46 |
| 2006/0200208 A1 | 9/2006 | Terry et al. | |
| 2006/0253161 A1 | 11/2006 | Libbus et al. | |
| 2007/0027496 A1* | 2/2007 | Parnis | A61N 1/3601 607/42 |
| 2007/0073356 A1 | 3/2007 | Rooney et al. | |
| 2007/0191902 A1* | 8/2007 | Errico | A61N 1/36114 607/42 |
| 2007/0213771 A1* | 9/2007 | Spinner | A61N 1/36021 607/2 |
| 2008/0183248 A1* | 7/2008 | Rezai | A61N 1/0553 607/62 |
| 2008/0208305 A1 | 8/2008 | Rezai et al. | |
| 2009/0155336 A1 | 6/2009 | Rezai | |
| 2009/0204173 A1 | 8/2009 | Fang et al. | |
| 2009/0281593 A9 | 11/2009 | Errico et al. | |
| 2010/0023088 A1 | 1/2010 | Stack et al. | |
| 2010/0070004 A1 | 3/2010 | Hlavka et al. | |
| 2010/0094376 A1 | 4/2010 | Penner et al. | |
| 2010/0114261 A1 | 5/2010 | Errico et al. | |
| 2010/0191311 A1* | 7/2010 | Scheiner | A61N 1/0556 607/62 |
| 2010/0217347 A1* | 8/2010 | Swoyer | A61N 1/3601 607/42 |
| 2010/0228310 A1* | 9/2010 | Shuros | A61N 1/0551 607/17 |
| 2010/0241190 A1 | 9/2010 | Kilgore et al. | |
| 2010/0324630 A1* | 12/2010 | Lee | A61N 1/06 607/76 |
| 2011/0009927 A1 | 1/2011 | Parker et al. | |
| 2011/0118725 A1 | 5/2011 | Mayse et al. | |
| 2011/0125216 A1 | 5/2011 | Kilgore et al. | |
| 2011/0184486 A1 | 7/2011 | De Ridder | |
| 2012/0059437 A1 | 3/2012 | Shalev | |
| 2012/0172680 A1 | 7/2012 | Gelfand et al. | |
| 2012/0221087 A1 | 8/2012 | Parnis et al. | |
| 2013/0138193 A1* | 5/2013 | Durand | A61N 1/36071 607/118 |
| 2013/0289678 A1 | 10/2013 | Clark et al. | |
| 2014/0018788 A1 | 1/2014 | Engelman et al. | |
| 2014/0364921 A1 | 12/2014 | Legay et al. | |
| 2014/0364923 A1 | 12/2014 | Legay et al. | |
| 2015/0202444 A1 | 7/2015 | Franke et al. | |
| 2015/0202446 A1 | 7/2015 | Franke et al. | |

FOREIGN PATENT DOCUMENTS

| | | |
|---|---|---|
| CN | 101048194 A | 10/2007 |
| CN | 101657230 A | 2/2010 |
| CN | 101972513 A | 2/2011 |
| CN | 103372262 A | 10/2013 |
| CN | 106573139 A | 4/2017 |
| CN | 106573143 A | 4/2017 |
| CN | 106573144 A | 4/2017 |
| CN | 106573145 A | 4/2017 |
| CN | 106573143 B | 2/2019 |
| EP | 3094369 B1 | 1/2018 |
| EP | 3094366 B1 | 6/2018 |
| JP | 2006508768 A | 3/2006 |
| JP | 2011502022 A | 1/2011 |
| JP | 2011502586 A | 1/2011 |
| JP | 2017502786 A | 1/2017 |
| JP | 2017502787 A | 1/2017 |
| JP | 6484637 B2 | 2/2019 |
| KR | 20120126140 A | 11/2012 |
| KR | 1020120126140 A | 11/2012 |
| WO | WO-2007103324 A1 | 9/2007 |
| WO | WO-2009058258 A1 | 5/2009 |
| WO | WO-2009061813 A1 | 5/2009 |
| WO | WO-2010019481 A1 | 2/2010 |
| WO | WO-2012021583 A1 | 2/2012 |
| WO | WO-2013018083 A2 | 2/2013 |
| WO | WO-2015109015 A1 | 7/2015 |
| WO | WO-2015109018 A1 | 7/2015 |
| WO | WO-2015109023 A1 | 7/2015 |
| WO | WO-2015109024 A1 | 7/2015 |

OTHER PUBLICATIONS

Bhakta, Bipin B, et al., "Management of spasticity in stroke", British Medical Bulletin, 56 (No. 2), (2000), 476-485.

Canning, Brendan J., et al., "Evidence That Distinct Neural Pathways Mediate Parasympathetic Contractions and Relaxations of Guinea-Pig Trachealis", Journal of Physiology (1993), 471, (1993), 25-40.

Canning, Brendan J., "Reflex regulation of airway smooth muscle tone", J Appl Physiol 101, (2006), 971-985.

Chang, C. C., et al., "Mechanisms of the inhibition by neostigmine of tetanic contraction in the mouse diaphragm", Br. J. Pharmac. 87, (1986), 757-762.

Coleridge, H M, et al. "Characteristics of C Fibre Baroreceptors in the Carotid Sinus of Dogs", J. Physiol, (1987), 394, (1987), 291-313.

Franke, Manfred, et al., "Depletion Block To Block Nerve Communication", U.S. Appl. No. 61/928,725, filed Jan. 17, 2014.

(56) References Cited

OTHER PUBLICATIONS

Franke, Manfred, et al., "Selective Nerve Stimulation Using Presynaptic Terminal Depletion Block", U.S. Appl. No. 61/928,732, filed Jan. 17, 2014.
Franke, Manfred, et al., "Systems And Methods For Delivering Pulmonary Therapy", U.S. Appl. No. 61/928,714, filed Jan. 17, 2014.
Franke, Manfred, et al., "Systems And Methods For Selective Stimulation Of Nerve Fibers In Carotid Sinus", U.S. Appl. No. 61/928,707, filed Jan. 17, 2014.
Gosens, Reinoud, et al., "Muscarinic receptor signaling in the pathophysiology of asthma and COPD", Respiratory Research 2006, 7:73, (2006), 1-15.
Hoffman, Thomas J., et al., "Inhibition of Histamine-Induced Bronchoconstriction in Guinea Pig and Swing by Pulsed Electrical Vagus Nerve Stimulation", Neuromodulation vol. 12; No. 4, (2009), 261-269.
Hoffman, Thomas J., et al., "Low Voltage Vagal Nerve Stimulation Reduces Bronchoconstriction in Guinea Pigs Through Catecholamine Release", Neuromodulation. 2012 ; 15(6), (2012). 527-536.
Kilgore, K L, et al., "Nerve conduction block utilising high-frequency alternating current", 14 pgs.
Kilgore, Kevin, et al., "Combined Direct Current and High Frequency Nerve Block for Elimination of the Onset Response", 31st Annual International Conference of the IEEE EMBS, Minneapolis, Minnesota, USA, Sep. 2-6, 2009, (2009), 197-199.
Kilgore, Kevin L, et al., "Reversible Nerve Conduction Block Using Kilohertz Frequency Alternating Current", Neuromodulation: Technology at the Neural Interface, (2013), 13 pgs.
Krzyzaniak, Michael J., et al., "Efferent vagal nerve stimulation attenuates acute lung injury following burn: The importance of the gut-lung axis", Surgery; 150(3):, (Sep. 2011), 379-389.
Lopez, Nicole E, et al., "Vagal Nerve Stimulation Blocks Peritoneal Macrophage Inflammatory Responsiveness after Severe Burn Injury", Shock. Aug. 2012 ; 38(3):, (Aug. 2012), 294-300.
Mokelke, Eric A., et al., "System and Method for Mapping Baroreceptors", U.S. Appl. No. 61/836,431, filed Jun. 18, 2013.
msu.edu, "Mechanism of Action of Bronchodilator Drugs", Link: http://cvm.msu.edu/research/research-labs/equine-pulmonary-laboratory/respiratory-diseases/heaves/mechanism-of-action-of-bronchodilator-drugs.
Paton, Julian, et al., "The Carotid Body as a Therapeutic Target for the Treatment of Sympathetically Mediated Diseases", Hypertension. 2013; 61, (2013), 5-13.
Rattay, Frank, "Electrical Nerve Stimulation Theory, Experiments and Applications", 26 pgs.
Seagard, J L, et al., "Firing characteristics of single-fiber carotid sinus baroreceptors.", Circulation Research Journal of The American Heart Association; 66:1499-1509, (1990), 12 pgs.
Sepulveda, P., et al., "Treatment of asthmatic bronchoconstriction by percutaneous low voltage nerve stimulation: case report", The Internet Journal of Asthma, Allergy and Immunology, vol. 7 No. 2, (2008).
Solomonow, M., et al., "Control of Muscle Contractile Force Through Indirect High-Frequency Stimulation", Amer. Journal of Physical Med.; vol. 62 No. 2, (1983), 71-82.
Strickland, Michael, et al., "Carotid Chemoreceptor Modulation of Regional Blood Flow Distribution During Exercise in Health and Chronic Heart Failure", Circulation Research. 100., (2007), 1371-1378.
Tkacova, Ruzena, "Systemic Inflammation in Chronic Obstructive Pulmonary Disease:May Adipose Tissue Play a Role? Review of the Literature and Future Perspectives", Mediators of Inflammation; vol. 2010, Article ID 585989, (2010), 1-12.
Undem, Bradley J., et al., "Autonomic Neural Control of Intrathoracic Airways", American Physiological Society; Comprehensive Physiology; 2, (2012), 1241-1267.
Undem, Bradley J., et al., "The Role of Vagal Afferent Nerves in Chronic Obstructive Pulmonary Disease", Proceedings of the American Thoracic Society vol. 2, (2005), 355-360.
Van Den Berge, M., et al., "Clinical and inflammatory determinants of bronchial hyperresponsiveness in COPD", Eur Respir J; 40:, (2012), 1098-1105.
Wine, Jeffrey J., et al., "Parasympathetic control of airway submucosal glands: Central reflexes and the airway intrinsic nervous system", Autonomic Neuroscience: Basic and Clinical 133, (2007), 35-54.
Wodlinger, Brian, et al., "Block of Peripheral Pain Response by High-Frequency Sinusoidal Stimulation", Neuromodulation; 16, (2013), 312-317.
Zhang, Yong, et al., "Ganglionated Plexi Ablation for Atrial Fibrillation", Basic Research and Clinical Applications, Prof. Jong-Il Choi (Ed.), ISBN: 978-953-307-399-6, InTech,, Available from: http://www.intechopen.com/books/atrial-fibrillation-basic-research-andclinical-applications/ganglionated-plexi-ablation-for-atrial-fibrillation, (2012), 239-255.
"U.S. Appl. No. 14/597,145, Final Office Action dated Nov. 10, 2016", 14 pgs.
"U.S. Appl. No. 14/597,145, Non Final Office Action dated May 16, 2016", 11 pgs.
"U.S. Appl. No. 14/597,145, Response filed Aug. 16, 2016 to Non Final Office Action dated Aug. 16, 2016", 10 pgs.
"Australian Application Serial No. 2015206540, Office Action dated Nov. 7, 2016", 3 pgs.
"Australian Application Serial No. 2015206541, First Examiners Report dated Oct. 11, 2016", 3 pgs.
"International Application Serial No. PCT/US2015/011458, International Preliminary Report on Patentability dated Jul. 28, 2016", 7 pgs.
"International Application Serial No. PCT/US2015/011458, International Search Report dated Mar. 31, 2015", 3 pgs.
"International Application Serial No. PCT/US2015/011458, Written Opinion dated Mar. 31, 2015", 5 pgs.
"International Application Serial No. PCT/US2015/011461, International Preliminary Report on Patentability dated Jul. 28, 2016", 8 pgs.
"International Application Serial No. PCT/US2015/011461, International Search Report dated Mar. 27, 2015", 6 pgs.
"International Application Serial No. PCT/US2015/011461, Written Opinion dated Mar. 27, 2015", 7 pgs.
"International Application Serial No. PCT/US2015/011467, International Preliminary Report on Patentability dated Jul. 28, 2016", 10 pgs.
"International Application Serial No. PCT/US2015/011467, International Search Report dated Mar. 26, 2015", 5 pgs.
"International Application Serial No. PCT/US2015/011467, Written Opinion dated Mar. 26, 2015", 8 pgs.
"International Application Serial No. PCT/US2015/011468, International Preliminary Report on Patentability dated Jul. 28, 2016", 9 pgs.
"International Application Serial No. PCT/US2015/011468, International Search Report dated Mar. 30, 2015", 5 pgs.
"International Application Serial No. PCT/US2015/011468, Written Opinion dated Mar. 30, 2015", 7 pgs.
Fisher, Karen M., et al., "Blocking central pathways in the primate motor system using high-frequency sinusoidal current", J Neurophysiol 113(5): 1670-1680, Mar. 1, 2015.
Franke, Manfred, "Translating Electric KHFAC and DC Nerve Block from Research to Application", Thesis • May 2014, 199 pages.
Ishii, Koji, et al., "Effects of Neostigmine on Bronchoconstriction With Continuous Electrical Stimulation In Rats", Journal of Anesthesia, Springer-Verlag, TO, vol. 26, No. 1, (Nov. 1, 2011), 80-84.
Stretton, C, et al., "Sensory Nerve Depletion Potentiates Inhibitory Non-Adrenergic, Non-Cholinergic Nerves In Guinea-Pig Airways", European Journal of Pharmacology, Elsevier Science, NL, vol. 184, No. 2-3, (Aug. 10, 1990), 333-337.
Wedensky, N. E., "Die Erregung, Hemmung und Narkose (The excitation, inhibition and Narkose)", Archiv für die gesamte Physiologie des Menschen und der Tiere, 1903. 100: p. 1-144 (With Machine Translation).

(56) References Cited

OTHER PUBLICATIONS

Wedensky, N. E., "Ueber einige Beziehungen zwischen der Reizstarke und der Tetanushohe bei indirecter Reizung Over some relations between the attraction strength and the Tetanushöhe when indireeter provoking", Archiv für die gesamte Physiologic des Menschen und der Tiere of Dr. E.F.W. Pflüger, 37: p. 69-72, Dec. 1885 (With Machine Translation).

"U.S. Appl. No. 14/597,112, Non Final Office Action dated Jan. 13, 2017", 10 pgs.

"U.S. Appl. No. 14/597,112, Response filed Apr. 13, 2017 to Non Final Office Action dated Jan. 13, 2017", 9 pgs.

"U.S. Appl. No. 14/597,145, Non Final Office Action dated Mar. 1, 2017", 14 pgs.

"U.S. Appl. No. 14/597,145, Response filed Feb. 10, 2017 to Final Office Action dated Nov. 10, 2016", 9 pgs.

"Australian Application Serial No. 2015206540, Response filed Apr. 6, 2017 to Office Action dated Nov. 7, 2016", 12 pgs.

"European Application Serial No. 15701907.6, Response filed Mar. 24, 2017 to Communication Pursuant to Rules 161(1) and 162 EPC dated Sep. 22, 2016", 7 pgs.

"European Application Serial No. 15701908.4, Response filed Apr. 10, 2017 to Communication Pursuant to Rules 161(1) and 162 EPC dated Sep. 30, 2016", 7 pgs.

"European Application Serial No. 15701910.0, Response filed Apr. 3, 2017 to Communication Pursuant to Rules 161(1) and 162 EPC dated Oct. 5, 2016", 14 pgs.

"European Application Serial No. 15702608.9, Response filed Mar. 29, 2017 to Communication Pursuant to Rules 161(1) and 162 EPC dated Sep. 21, 2016", 9 pgs.

"U.S. Appl. No. 14/597,112, Advisory Action dated Oct. 20, 2017", 4 pgs.

"U.S. Appl. No. 14/597,112, Final Office Action dated Jul. 12, 2017", 10 pgs.

"U.S. Appl. No. 14/597,112, Pre-Appeal Brief Request filed Nov. 13, 2017", 5 pgs.

"U.S. Appl. No. 14/597,112, Response filed Sep. 12, 2017 to Final Office Action dated Jul. 12, 2017", 11 pgs.

"U.S. Appl. No. 14/597,137, Advisory Action dated Jan. 3, 2018", 3 pgs.

"U.S. Appl. No. 14/597,137, Final Office Action dated Oct. 23, 2017", 13 pgs.

"U.S. Appl. No. 14/597,137, Non Final Office Action dated Mar. 26, 2018", 10 pgs.

"U.S. Appl. No. 14/597,137, Non Final Office Action dated Jun. 6, 2017", 16 pgs.

"U.S. Appl. No. 14/597,137, Notice of Allowance dated Sep. 25, 2018", 10 pgs.

"U.S. Appl. No. 14/597,137, Respone filed Jun. 26, 2018 to Non Final Office Action dated Mar. 26, 2018", 13 pgs.

"U.S. Appl. No. 14/597,137, Response filed Sep. 6, 2017 to Non Final Office Action dated Jun. 6, 2017", 12 pgs.

"U.S. Appl. No. 14/597,137, Response filed Dec. 13, 2017 to Final Office Action dated Oct. 23, 2017", 15 pgs.

"U.S. Appl. No. 14/597,145, 312 Amendment filed Nov. 8, 2018", 3 pgs.

"U.S. Appl. No. 14/597,145, Advisory Action dated Nov. 22, 2017", 6 pgs.

"U.S. Appl. No. 14/597,145, Examiner Interview Summary dated Apr. 16, 2018", 4 pgs.

"U.S. Appl. No. 14/597,145, Examiner Interview Summary dated Oct. 31, 2017", 3 pgs.

"U.S. Appl. No. 14/597,145, Final Office Action dated Aug. 30, 2017", 14 pgs.

"U.S. Appl. No. 14/597,145, Non Final Office Action dated Jan. 9, 2018", 15 pgs.

"U.S. Appl. No. 14/597,145, Notice of Allowance dated Apr. 30, 2019", 7 pgs.

"U.S. Appl. No. 14/597,145, Notice of Allowance dated Sep. 5, 2018", 5 pgs.

"U.S. Appl. No. 14/597,145, Notice of Allowance dated Dec. 26, 2018", 7 pgs.

"U.S. Appl. No. 14/597,145, PTO Response to Rule 312 Communication dated Nov. 14, 2018", 2 pgs.

"U.S. Appl. No. 14/597,145, Response filed Jun. 1, 2017 to Non Final Office Action dated Mar. 1, 2017", 11 pgs.

"U.S. Appl. No. 14/597,145, Response filed Oct. 30, 2017 to Final Office Action dated Aug. 30, 2017", 12 pgs.

"U.S. Appl. No. 14/597,145, Response filed Nov. 30, 2017 to Advisory Action dated Nov. 22, 2017", 14 pgs.

"Australian Application Serial No. 2015206541, Response filed Jul. 27, 2017 to First Examiners Report dated Oct. 11, 2016", 15 pgs.

"Chinese Application Serial No. 201580014596.3, Office Action dated Mar. 13, 2019", w/ English Summary, 4 pgs.

"Chinese Application Serial No. 201580014596.3, Office Action dated Aug. 8, 2018", W/ English Translation, 17 pgs.

"Chinese Application Serial No. 201580014596.3, Response filed Feb. 22, 2019 to Office Action dated Aug. 8, 2018", w/ English claims, 17 pgs.

"Chinese Application Serial No. 201580014596.3, Response Filed May 13, 2019 Office Action dated Mar. 13, 2019", w/English Claims, 10 pgs.

"Chinese Application Serial No. 201580014597.8, Office Action dated Jul. 3, 2018", w/ English translation, 11 pgs.

"Chinese Application Serial No. 201580014597.8, Response filed Nov. 16, 2018 to Office Action dated Jul. 3, 2018", w/ English claims, 21 pgs.

"Chinese Application Serial No. 201580014615.2, Office Action dated Mar. 21, 2019", w/ English translation, 16 pgs.

"Chinese Application Serial No. 201580014615.2, Office Action dated Jun. 28, 2018", W/ English summary, no translation sent, only brief summary from agent letter, 10 pgs.

"Chinese Application Serial No. 201580014615.2, Response filed Nov. 13, 2018 to Office Action dated Jun. 28, 2018", w/ English claims, 15 pgs.

"Chinese Application Serial No. 201580014615.2, Resposne Filed May 21, 2019 to Office Action dated Mar. 21, 2019", w/English Claims, 12 pgs.

"Chinese Application Serial No. 201580014616.7, Office Action dated Mar. 21, 2019", w/ English Translation, 20 pgs.

"Chinese Application Serial No. 201580014616.7, Office Action dated Jun. 28, 2018", w/ English translation, 21 pgs.

"Chinese Application Serial No. 201580014616.7, Response filed Nov. 13, 2018 to Office Action dated Jun. 28, 2018", w/ English claims, 17 pgs.

"European Application Serial No. 15702608.9, Communication Pursuant to Article 94(3) EPC dated Dec. 20, 2018", 4 pgs.

"European Application Serial No. 15702608.9, Response filed Apr. 23, 2019 to Communication Pursuant to Article 94(3) EPC dated Dec. 20, 2018", 15 pgs.

"Japanese Application Serial No. 2016-547078, Office Action dated May 29, 2018", w/ English translation, 4 pgs.

"Japanese Application Serial No. 2016-547078, Office Action dated Jul. 4, 2017", w/ English translation, 13 pgs.

"Japanese Application Serial No. 2016-547078, Response filed Aug. 17, 2018 to Office Action dated May 29, 2018", w/ English claims, claims were not amended in response, current claims from previous response filed included in attachment, 4 pgs.

"Japanese Application Serial No. 2016-547078, Response filed Dec. 27, 2017 to Office Action dated Jul. 4, 2017", w/ claims in English, 11 pgs.

"Japanese Application Serial No. 2016-547080, Office Action dated Apr. 3, 2018", w/ English translation, 9 pgs.

"Japanese Application Serial No. 2016-547080, Office Action dated Jun. 27, 2018", w/ English translation, 11 pgs.

"Japanese Application Serial No. 2016-547080, Office Action dated Dec. 25, 2018", w/ English translation, 12 pgs.

"Japanese Application Serial No. 2016-547080, Response filed Jul. 30, 2018 to Office Action dated Apr. 3, 2018", w/ English claims, 10 pgs.

(56) References Cited

OTHER PUBLICATIONS

"Japanese Application Serial No. 2016-547080, Response filed Oct. 13, 2017 to Office Action dated Jun. 27, 2017", w/ claims in English, 10 pgs.

* cited by examiner

SYSTEMS AND METHODS FOR DELIVERING PULMONARY THERAPY

CLAIM OF PRIORITY

This application claims the benefit of priority under 35 U.S.C. § 119(e) of U.S. Provisional Patent Application Ser. No. 61/928,714, filed on Jan. 17, 2014, which is herein incorporated by reference in its entirety.

CROSS REFERENCE TO RELATED APPLICATIONS

The following commonly-assigned U.S. patent application are related, are all filed on the same date as the present application, and are all herein incorporated by reference in their entirety: "Systems and Methods for Selective Stimulation of Nerve Fibers in Carotid Sinus," Ser. No. 61/928,707, filed on Jan. 17, 2014; "Depletion Block to Block Nerve Communication," Ser. No. 61/928,725, filed on Jan. 17, 2014; and "Selective Nerve Stimulation Using Presynaptic Terminal Depletion Block," Ser. No. 61/928,732, filed on Jan. 17, 2014.

TECHNICAL FIELD

This document relates generally to medical devices, and more particularly, to systems, devices and methods for delivering pulmonary therapies using a synaptic junction block.

BACKGROUND

Chronic bronchitis is a type of chronic obstructive pulmonary disease (COPD), and is characterized by chronic cough with sputum production. Airflow and gas exchange are significantly limited by airway inflammation, mucus hypersecretion, airway hyperresponsiveness, and eventual fibrosis of the airway walls. Asthma is similar to chronic bronchitis, though the underlying cause is often an inherent defect of airway smooth muscle or the inflammatory milieu, which makes airway smooth muscle hyperreactive. Chronic asthma can have similar airway wall thickening as in chronic bronchitis, leading to a permanent, irreversible airflow obstruction. Emphysema also is a type of COPD, and is characterized by the destruction of the lung parenchyma. This destruction of the lung parenchyma leads to a loss of elastic recoil and tethering which maintains airway patency. Because bronchioles are not supported by cartilage like the larger airways are, they have little intrinsic support and therefore are susceptible to collapse when destruction of tethering occurs, particularly during exhalation.

COPD currently affects over 15 million people in the United States alone and is currently the third leading cause of death in the country. Currently, over 90% of COPD cases are caused by inhalation of cigarette smoke. The economic and social burden of the disease is substantial and is increasing. Between about 50% and 75% of the economic burden for COPD is related to healthcare services for acute exacerbations of COPD (AECOPD). This economic burden is attributable mostly to emergency care and inpatient hospital care. AECOPD are defined by a sudden worsening of symptoms (e.g. increase in or onset of cough, wheeze, and sputum changes) that typically last for several days, up to a couple weeks. AECOPD are typically triggered by a bacterial infection, viral infection, or pollutants, which manifests quickly into airway inflammation, mucus hypersecretion, and bronchoconstriction, mucus production which cause significant airway restriction.

Despite relatively efficacious drugs (long-acting muscarinic antagonists, long-acting beta agonists, corticosteroids, and antibiotics) that treat COPD symptoms, a particular segment of patients known as "frequent exacerbators" often visit the emergency room and hospital with exacerbations and also have a more rapid decline in lung function, poorer quality of life, and greater mortality. A need exists for COPD patients to reduce the occurrence of AECOPD events.

The autonomic nervous system provides constant control over airway smooth muscle, secretory cells, and vasculature. Parasympathetic fibers are motor to bronchial smooth muscle, inhibitory to the pulmonary vessels, and secretory to the bronchial glands; and sympathetic fibers are inhibitory to the bronchial muscle, motor to the pulmonary vessels, and inhibitory to aveolar glands. Although both sympathetic and parasympathetic branches of the autonomic nervous system innervate the airways, parasympathetic branch dominates especially with respect to control of airway smooth muscle and mucus secretions. Cholinergic nerve fibers arise in the nucleus ambiguous in the brain stem and travel down the vagus nerve (right and left vagus nerves) and synapse in parasympathetic ganglia which are located within the airway wall. These parasympathetic ganglia are most numerous in the trachea and mainstem bronchi, especially near the hilus and points of bifurcations, with fewer ganglia smaller in size dispersed in distal airways. From these ganglia short postganglionic fibers travel to airway smooth muscle and submucosal glands. Cholinergic control of airway smooth muscle involves pre-ganglionic and post-ganglionic parasympathetic nerves releasing acetylcholine (ACh) and can be activated by airway and extra-pulmonary afferent nerves. ACh is released from post-ganglionic fibers and acts upon M1-and M3-receptors on smooth muscles and submucosal glands to cause bronchoconstriction and mucus secretion, respectively. ACh may regulate airway inflammation and airway remodeling, which may contribute to the pathophysiology of obstructive airways diseases. Therefore controlling the parasympathetic nerve signals to the lungs can control bronchoconstriction, mucus secretion, cough, and possibly inflammation and remodeling.

A wide variety of stimuli (cigarette smoke, mechanical stimuli, and other irritants) are able to elicit reflex cholinergic bronchoconstriction through activation of sensory receptors in the larynx or airways. Said sensory receptors primarily include rapidly adapting receptors (RARs) and C-Fibers, both of which have nerve endings in the epithelium. Activation of these afferent nerves causes a cholinergic reflex that is known to result in bronchoconstriction and an increase in airway mucus secretion through the activation of muscarinic receptors on airway smooth muscle cells and submucosal glands. Irritants in the airways can trigger afferent receptor nerves and set-off a reflex action initiating bronchoconstriction and mucus production, both of which are common during AECOPD events.

Anticholinergic drugs (antimuscarinic agents) such as Spiriva have been developed which are believed to bind to the muscarinic receptors on smooth muscle cells, preventing ACh from binding to those sites, resulting in a reduction in bronchoconstriction. These drugs are not completely effective for all patients (in part due to lack of compliance to treatment schedules) however, and many patients continue to have AECOPD events despite being prescribed these drugs.

Bronchial hyperreactivity (BHR) is common in COPD and is most likely caused by hypersensitivity of receptor nerve fibers, lower thresholds for reflex action initiation, and reduced natural self-limitation mechanism of ACh release. Various reports have suggested that BHR may be present in over 60% to of COPD patients. This "hyperreactivity" may be due to a "hyperreflexivity". There are several mechanisms by which parasympathetic drive may be overactivated in inflammatory disease. Inflammation is commonly associated with overt activation and increases in excitability of vagal C-fibers in the airways that could increase reflex parasympathetic tone. Also, airway inflammation and inflammatory mediators have been found to increase synaptic efficacy and decrease action potential accommodation in bronchial parasympathetic ganglia; effects that would likely reduce their filtering function and lead to prolonged excitation. Further, airway inflammation has also been found to inhibit muscarinic M2 receptor-mediated auto-inhibition of ACh release from postganglionic nerve terminals. This would lead to a larger end-organ response (e.g. smooth muscle contraction) for a given amount of action potential discharge. Additionally, airway inflammation has been associated with phenotypic changes in the parasympathetic nervous system that could affect the balance of cholinergic contractile versus non-adrenergic non-cholinergic (NANC) relaxant innervation of smooth muscle.

In addition to smooth muscle contraction and mucus production noted above, chronic inflammation of the airways plays a central role in COPD. Even during stable COPD, increases in the number of inflammatory proteins have been described in the systemic circulation, including C-reactive protein (CRP), tumor necrosis factor-alpha (TNF-$\alpha$), interleukin (IL)-6 and IL-8. Small but significant increases in circulating levels of both the soluble TNF receptors 55 and 75 (sTNF-R55 and sTNF-R75), IL-10 and IL-18 have also been reported in such patients. Importantly, epidemiological studies suggesting relationships between circulatory inflammatory mediators and reductions in pulmonary functions reflected by decreases in forced expiratory volume in one second (FEV1). COPD exacerbations are associated with further increases in these inflammatory markers of both bronchial and systemic inflammation over and above levels present during the stable state of the disease. A need therefore additionally exists to reduce inflammation of the airways in COPD patients.

SUMMARY

Some embodiments disclosed herein provide a reversible synaptic junction block, which may also be referred to as a depletion block, to targeted nerves to reduce parasympathetic drive. The reduced parasympathetic drive may be used to alleviate symptoms of pulmonary disease.

An example of a system may include an electrode and a pulse generation system. The electrode may be configured to be implanted near a neural target that innervates airways. The pulse generation system may be configured to be operably connected to the electrode to deliver depletion block stimulation through the electrode to alleviate symptoms of pulmonary disease. The pulse generation system and the electrode may be configured to cooperate to capture axons in the neural target. The depletion block stimulation may include a series of pulses at a depletion pulse frequency within a range between about 100 Hz to about 1 kHz (e.g. 100 Hz to 1000 Hz or frequencies near that range to provide the depletion block).

An example of a method may deliver depletion block stimulation, using an implanted electrode, to a neural target that innervates airways. Delivering the depletion block stimulation may include delivering a series of electrical pulses at a depletion pulse frequency where the depletion pulse frequency is within a range between about 100 Hz to about 1 kHz.

An example of a method may implant an electrode in or near an airway and proximate a neural target that innervates airways, and deliver depletion block stimulation, using the implanted electrode, to a neural target that innervates airways. Delivering the depletion block stimulation may include delivering a series of electrical pulses at a depletion pulse frequency where the depletion pulse frequency is within a range between about 100 Hz to about 1 kHz.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
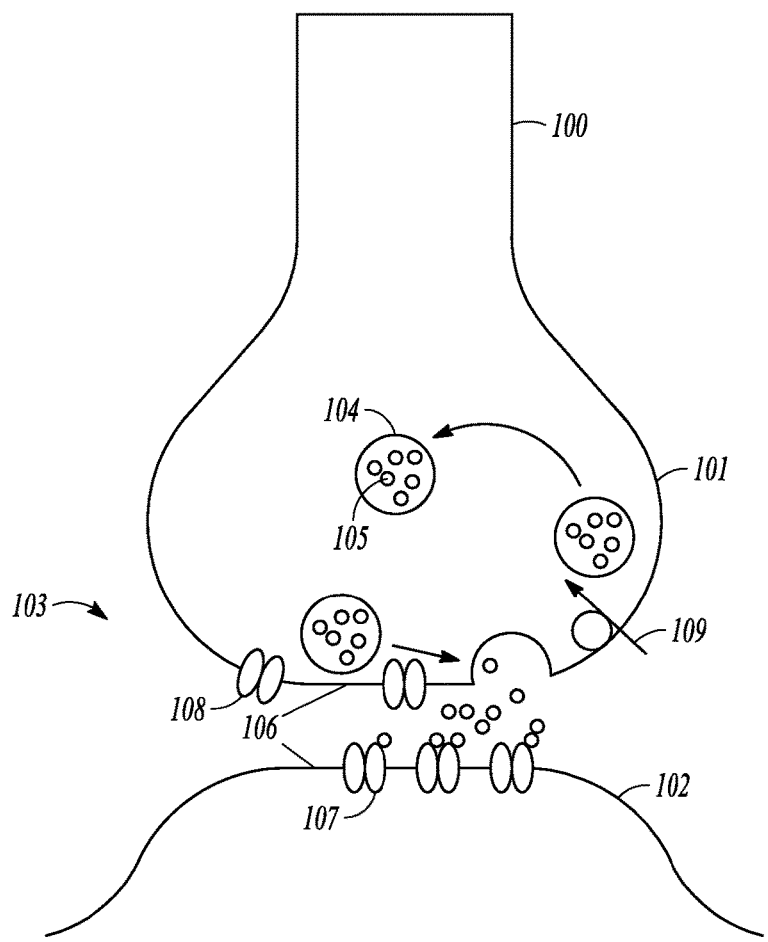
FIG. 1 illustrates neural activity at a synapse between a nerve and another membrane.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Some embodiments disclosed herein provide a reversible synaptic junction block ("depletion block") to targeted nerves to reduce parasympathetic drive for the purpose of alleviating symptoms of pulmonary disease. The discussion that follows provides a general discussion of the technique for creating a reversible synaptic junction block along with a general discussion of the autonomic nervous system (ANS) including the vagus nerve and branches from the vagus. Then, this disclosure discusses examples of applications for alleviating symptoms of pulmonary disease. These applications include electrode(s) within airways to deliver the depletion block to the neural targets, leads positioned adjacent or wrapped around airways to operably position electrode(s) to deliver the depletion block to the neural targets, and vagal nerve stimulation to deliver the depletion block to the neural targets.

Reversible Synaptic Junction Block ("Depletion Block") and ANS

Nerve fibers, also referred to as axons, are projections from nerve cells. A nerve fiber connects a nerve cell to another nerve cell or to muscle or to gland cells at synapses. Synapses are structures that permit nerve cells to pass an electrical or chemical signal to other cells. Nerve fibers includes A fibers, B fibers, and C fibers. A fibers are the largest and, generally, the first captured as stimulation amplitude increases. A fibers can be sensory fibers (afferent) or motor fibers (efferent) that innervate muscle tissue. For example, stimulation of the vagus nerve in the cervical region may excite laryngeal muscle fibers which causing laryngeal activation which may be used as a marker for capture of the vagus nerve. B fibers are smaller and next to be captured when increasing amplitude. These are typically efferent parasympathetic and sympathetic fibers. These B fibers may be a target for an autonomic neural stimulation therapy. C fibers are the smallest and associated with pain and other sensory information.

It has been observed that thicker nerve fibers are generally activated before thinner nerve fibers. Thick nerve fibers have longer sections of myelin sheaths between the nodes of Ranvier where the depolarization occurs and thus the change in electric field they experience is greater. It is currently believed that the vagus nerve includes the fiber types and sizes illustrated in Table 1, and it is further believed that the majority of the fibers are C fibers.

TABLE 1

Vagal Nerve Fibers

| Fibers | Origin | Size (um) | Conduction Velocity (m/s) | Innervation |
|---|---|---|---|---|
| Aα | Motor | 13-20 | 80-120 | Larynx |
| Aγ | Motor | 5-8 | 4-24 | |
| Aα | Sensory | 13-20 | 80-120 | All organs |
| Aβ | Sensory | 6-12 | 33-75 | larynx and airways |
| Aδ | Sensory | 1-5 | 3-30 | lungs, heart |
| B (pre-g) | Efferent | 1-5 | 3-15 | stomach, pancreas |
| C (pos-g) | Efferent | 0.2-1.5 | 0.5-2 | bladder |
| C | Sensory | 0.2-1.5 | 0.5-2 | |

Some proposed autonomic neural stimulation therapies attempt to capture as many nerve fibers in the vagus nerve as possible by titrating amplitude up as high as tolerable. In general terms vagal stimulation may first capture A motor and large sensory nerves fibers, then small sensory and B parasympathetic nerve fibers. This order is a general order because fibers that are closer to the electrodes experience a stronger electric field and are activated before fibers that are further away, and further these fiber types overlap in their size. The fibers that drive heart rate down are the smallest B efferent parasympathetic fibers. These B efferent parasympathetic fibers are the smallest of the myelinated fibers, as the C fibers are unmyelinated. Neural stimulation that causes a heart rate response indicates that the B efferent parasympathetic fibers have been captured and that the other larger fiber types are also being captured.

FIG. 1 illustrates neural activity at a synapse between a nerve and another membrane. An action potential propagates electrically down nerve axon 100 until it reaches a nerve ending, which may be referred to as a presynaptic terminal 101. The presynaptic terminal communicates with a post-synaptic membrane 102 of a target cell. The target cell may be another nerve or a muscle or gland. This membrane-tomembrane junction of the presynaptic terminal and the target cell is referred to as a synapse 103. A type of synapse is an electrical synaptic junction where the presynaptic terminal electrically communicates with the postsynaptic membrane using ions or small molecules that pass through channels from one cell to the next. Another type of synapse is a chemical synaptic junction, where neurotransmitters are used to transmit between cells. The presynaptic area 101 has a large number of synaptic vesicles 104 that contain neurotransmitter chemicals 105. Action potentials that propagate to the presynaptic terminal 101 drive a chemical reaction in the presynaptic terminal that releases neurotransmitters from synaptic vesicles within the terminal into the extracellular space. This extracellular space may be referred to as a synaptic cleft 106. The neurotransmitters cross the synaptic cleft between the presynaptic and postsynaptic terminals. The neurotransmitters start a chain of reaction in receptors 107 of either the post-synaptic membrane 102 (another neuronal cell) or the muscle cells (neuromuscular junction) that trigger either the firing of an action potential in the post-synaptic neuron or the muscular contraction if the synapse ends in a neuromuscular junction. For example, where the target cell is a muscle and the synapse is a neuromuscular junction, the neurotransmitter acetylcholine (Ach) causes a rapid contraction of the target muscle cell. At a neuromuscular junction, the action potential travels to the neuromuscular synaptic junction, causing calcium ions to flow through voltage-gated calcium channels 108 which release Ach from the presynaptic terminal into the extracellular space. Postsynaptic receptors in the membrane of the target muscle cell receive the Ach. The presynaptic terminal has a neurotransmitter re-uptake pump 109 that replenishes the presynaptic terminal with synaptic vesicles of neurotransmitters.

The present inventors have observed that continual communication across this synaptic cleft 106 appears to require a minimal amount of time between action potentials in the nerve, having observed that post-synaptic receptors do not trigger action potentials if the pre-synaptic action potentials arrive close to each other. Higher stimulation frequencies will generate more stimulation pulses in a given period of time, and may generate more corresponding action potentials in the nerve during the period of time. For example, a neural stimulation signal may typically be within a range of about 0.25 Hz to 50 Hz (e.g. 20 Hz). At higher frequencies (e.g. about 100 Hz to about 1 kHz), it was observed that the presynaptic terminal was unable to communicate across the synaptic cleft even though action potentials continued to propagate through the axon. This inability of the presynaptic terminal to communicate may be referred to as a depletion block. The frequencies used to obtain this depletion block are lower than the high frequency (greater than 1 kHz) AC nerve block that would block action potentials from propagating down the nerve. At frequencies higher than 1 kHz, for example, the stimulation blocks the nerve from conducting the action potentials. In contrast, the depletion block is delivered at frequencies below 1 kHz and thus does not stop the action potentials from propagating down the nerve to the presynaptic terminal, but rather depletes the presynaptic terminal so it is no longer able to communicate across the synaptic cleft to receptors of another cell.

Figure 2:
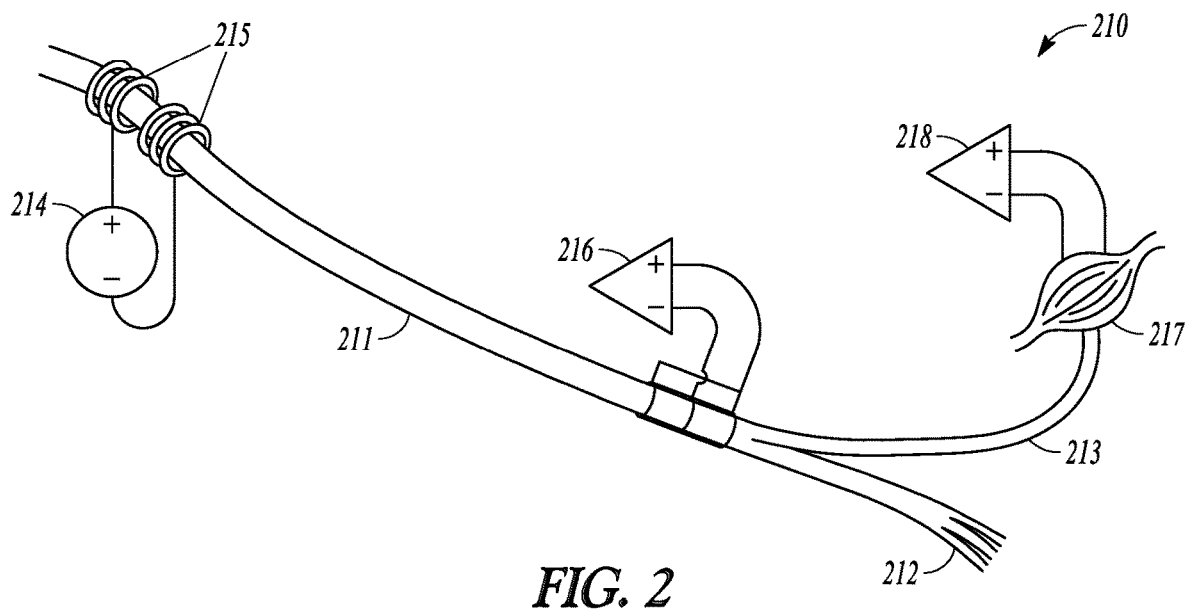
FIG. 2 illustrates an experimental setup used to observe a presynaptic terminal depletion block.

FIG. 2 illustrates an experimental setup 210 used to observe a presynaptic terminal depletion block. A cervical vagus nerve 211 branches into the thoracic branch 212 and the recurrent laryngeal nerve 213. The illustrated experimental setup was used to stimulate the cervical vagus nerve 211 using a current source 214 and helical electrodes 215 in a bipolar arrangement, to monitor neural activity before the cervical vagus nerve 211 branches into the recurrent laryngeal nerve branch 213 and the thoracic branch 212 using an electroneurography (ENG) monitor 216, and to monitor vibration of the laryngeal muscles 217 using an electromyography (EMG) monitor 218. This set up was used to observe that action potentials from depletion block stimulation were still sensed by the ENG, but laryngeal vibrations were not sensed by the EMG 218. Thus, it could be concluded that the depletion block stimulation blocked the ability of the presynaptic terminal to communicate across the synaptic cleft. The concept for achieving the depletion block of the neuromuscular junction may be implemented to provide neurosynaptic blocks which may be useful for nerves that innervate bronchi (e.g. block afferent (sensory) information from the bronchi to the spinal cord and brain).

Figure 3:
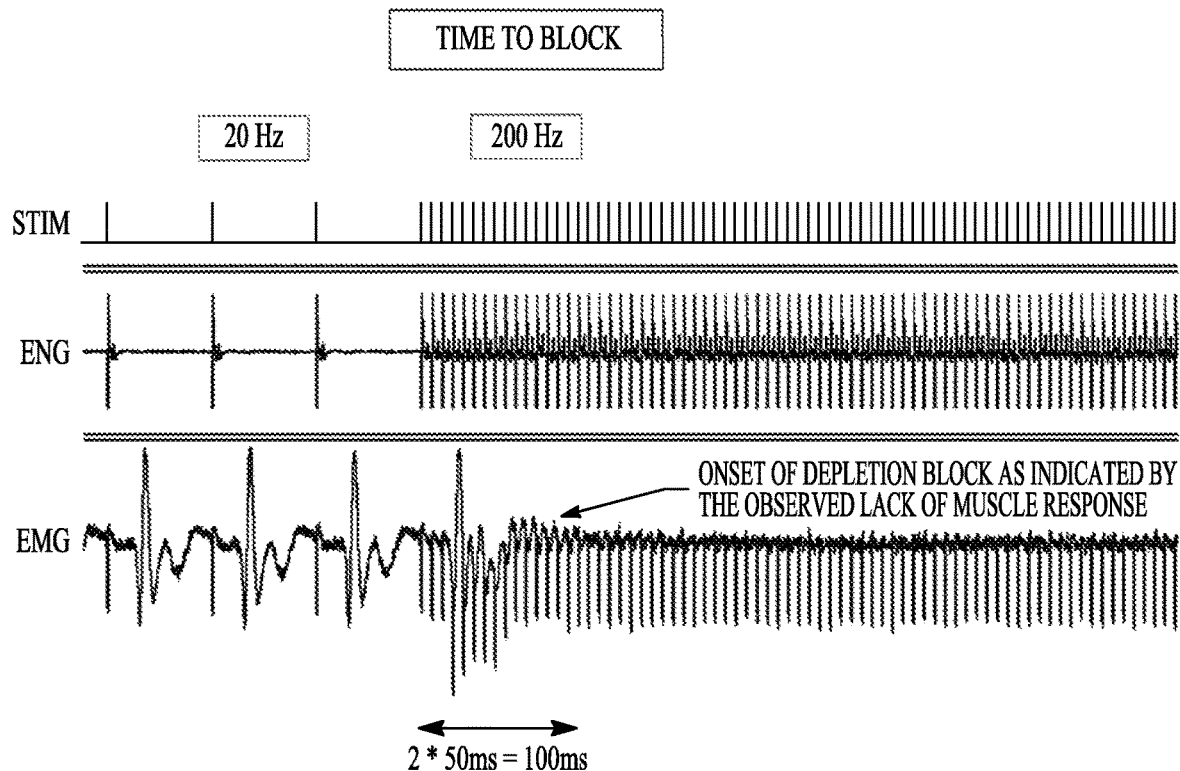
FIG. 3 illustrates the observed relationship between the stimulus signal and the recorded ENG and EMG signals when the stimulus changes from 20 Hz to 200 Hz, and also includes the observed time to deplete the presynaptic terminal and block the synaptic junction.

FIG. 3 illustrates the observed relationship between the stimulus signal and the recorded ENG and EMG signals when the stimulus changes from 20 Hz to 200 Hz, and also includes the observed time to deplete the presynaptic terminal and block the synaptic junction. During the 20 Hz stimulation, both the ENG and EMG signals follow the stimulus signal. The high peaks in both ENG and EMG signals reflect the stimulation artifact. However, during the 200 Hz stimulation, the ENG response is still present after the stimulus signal but the EMG signal quickly subsides after an onset response of about 100 ms. After a brief transitional period after the stimulus changes to 200 Hz, only the artifact from charge-balancing is seen in the EMG waveform. Thus, the axons in the nerve continue to be active by propagating action potentials, but the communication across the synaptic cleft is reduced or stopped after the presynaptic terminal has been depleted from its ability to communicate across the synaptic cleft. As illustrated, this synaptic junction block occurs very quickly (e.g. 50 to 100 ms after the 200 Hz signal is applied), as soon as the propagated pulses received at the presynaptic terminal deplete the presynaptic terminal from its ability to communicate. It does not appear that the physiological reuptake process that restores neurotransmitters and/or calcium in the presynaptic terminal can keep up with the transmission of the neurotransmitters from the 200 Hz stimulation.

Figure 4:
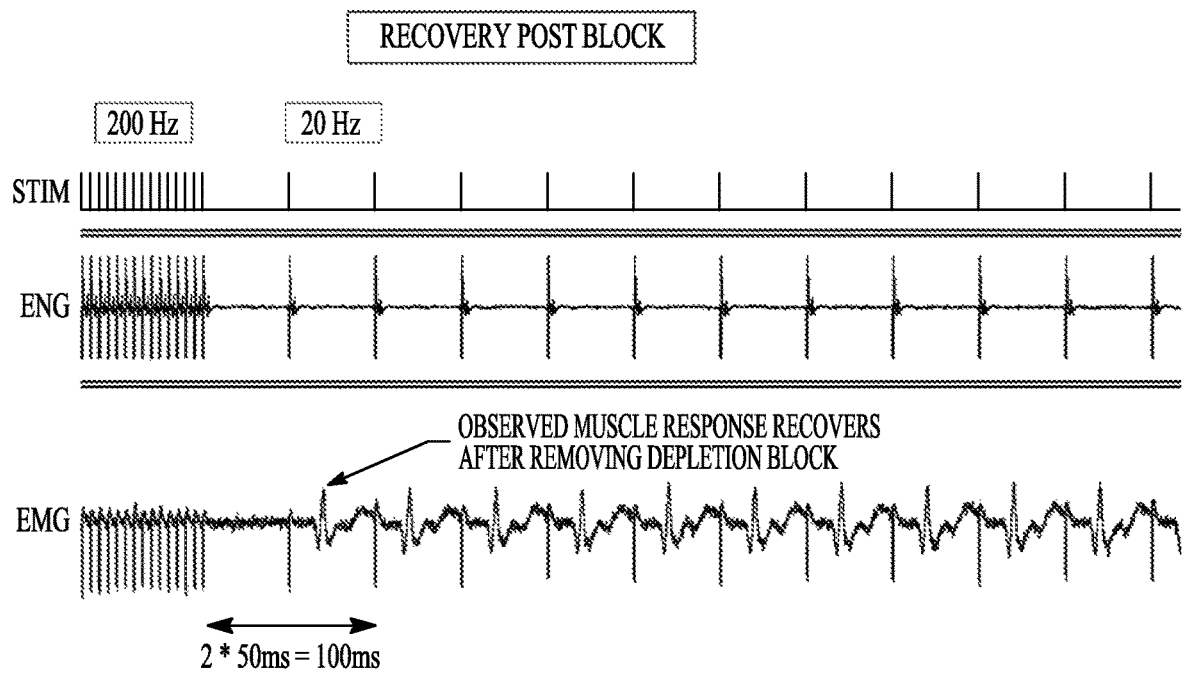
FIG. 4 illustrates the relationship between the stimulus signal and the recorded ENG and EMG signals when the stimulus changes from 200 Hz to 20 Hz.

FIG. 4 illustrates the relationship between the stimulus signal and the recorded ENG and EMG signals when the stimulus changes from 200 Hz to 20 Hz. The synaptic junction block occurs when the stimulus is delivered at 200 Hz. During this time, the ENG is still present following the stimulus artifact signal but the EMG response is not present. This indicates that the stimulus is capturing the nerve and causing action potentials to propagate through the axon. Every pulse in the stimulation causes a respective action potential in the nerve fiber. However, the laryngeal muscle is not stimulated because of the presynaptic terminal depletion that causes the synaptic junction block. The 200 action potentials per second deplete the ability of the presynaptic terminal to communicate across the synaptic cleft. When the stimulus changes from 200 Hz to 20 Hz, however, the ENG response continues to be present following the stimulus pulse as every pulse in the stimulation causes a respective action potential in the nerve fiber. The EMG reappears right after the stimulus pulse just after a brief transitional period after the stimulation frequency changes to 20 Hz. The ability of the presynaptic terminal to communicate across the synaptic cleft is not depleted by 20 pulses per second. Thus, as illustrated, the synaptic junction block can be removed very quickly (e.g. 50 ms to 100 ms after the signal changes from 200 Hz to 20 Hz signal), which is believed to reflect the physiological response time for restoring neurotransmitters and/or calcium in the presynaptic terminal.

As illustrated in Table 2, it was observed that certain frequencies turned the depletion block of the synaptic junction on/off more quickly than other frequencies. Data suggest that frequencies greater than about 200 Hz provide a fast depletion block, whereas frequencies between about 100 to about 150 Hz provides slower depletion blocks. Frequencies below 100 Hz tend not be effective to provide the depletion block, as those frequencies do not exceed the ability of the presynaptic terminal to restore its ability to communicate from the presynaptic terminal across the synaptic cleft to the target cell. In a neural muscular junction, for example, frequencies less than about 100 Hz cause tetanic contraction; frequencies between about 100 to about 150 Hz causes a 90% depletion block in about 10 seconds to 4 seconds; a frequency between about 200 Hz to 1000 Hz causes a 90% depletion block; and a frequency is greater than 1 kHz starts to enter into nerve conduction block where the stimulation arrests the actions potentials from propagating down the nerve.

TABLE 2

| | Freq (Hz) | Time to 90% Block (sec) | | Percentage of unblocked EMG (%) | |
|---|---|---|---|---|---|
| | | mean | stdev | mean | stdev |
| Activation | 40[1] | — | — | 110 | 13.18 |
| | 70[1] | — | — | 39 | 8.42 |
| Slow Block | 100*,[2] | 10.74 | 2.2 | 8.2 | 3.77 |
| | 130[1] | 9.33 | 0.55 | 4.38 | 1.06 |
| | 150[2] | 4.43 | 2.59 | 3.88 | 1.13 |
| Fast Block | 200[2] | 0.53 | 0.16 | 2.25 | 1.04 |
| | 260[1] | 0.16 | 0.05 | 0.75 | 0.89 |
| | 300[2] | 0.13 | 0.05 | 1.13 | 1.13 |
| | 400[1] | 0.14 | 0.05 | 0.63 | 0.74 |

Randomized study; n = 8 (100 Hz: n = 5), data from 2 * N = 1

Figure 5A:
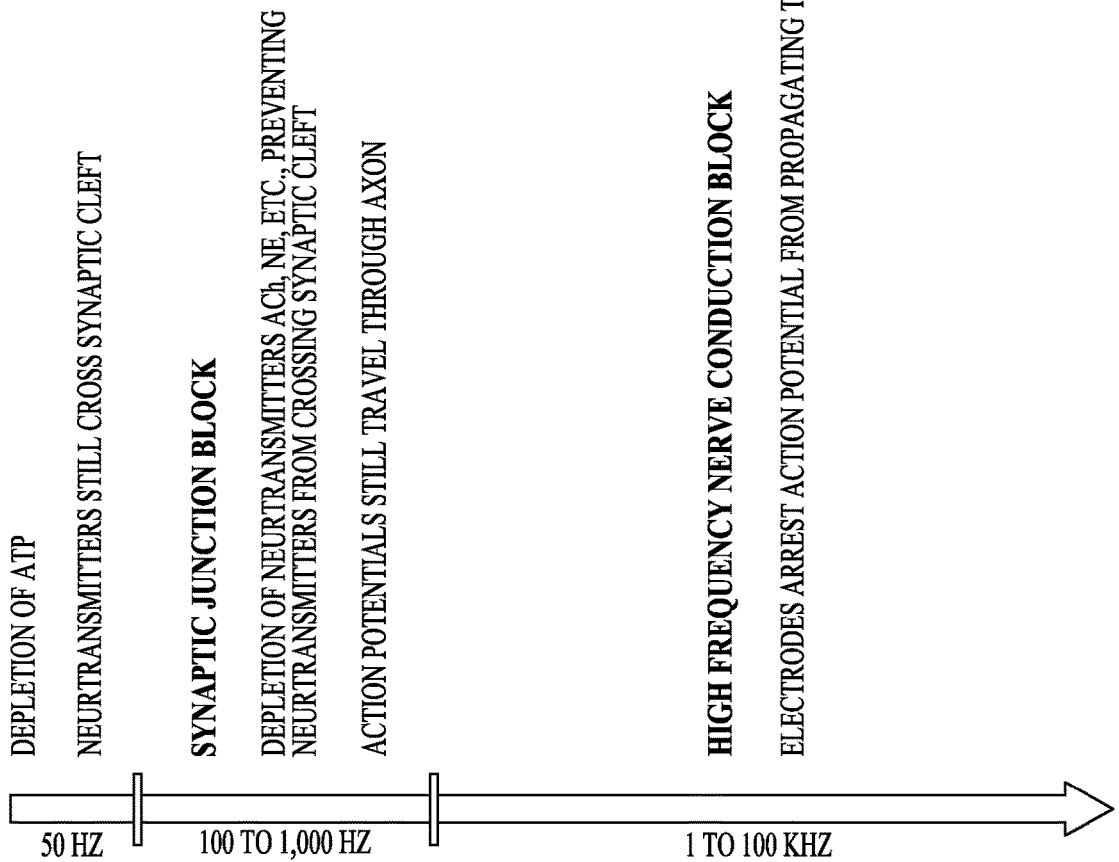
FIGS. 5A and 5B illustrate the response of a neural muscular junction to different stimulation frequencies.

FIG. 5A illustrates the response of a neural muscular junction to different stimulation frequencies. The neural muscular junction is a type of synaptic junction where an axon in a nerve communicates with muscle. Stimulation of axons within a range generally below 100 Hz (e.g. about 50 Hz) may cause a tetanic contraction of the muscle. Eventually, the muscle may fatigue and no longer respond to additional stimulation. The presynaptic terminal is depleted from its ability to communicate across the synaptic cleft at stimulation frequencies within a range from about 100 Hz to about 1 kHz. This frequency of the stimulation signal is outside of the ability of the physiological system to trigger the muscular contraction, as the frequency may cause the action potentials to arrive faster than the neurotransmitters and/or calcium can be replenished for subsequent action potentials in the stimulation. The observed block is attributable to a depletion of the junction but not fatigue of the muscle. Thus, a benefit of the depletion block applied to neural muscular junctions is that the depletion block does not cause muscle fatigue or tetanic contraction. The neuromuscular depletion block is quickly reversible by stopping stimulation.

Figure 5B:
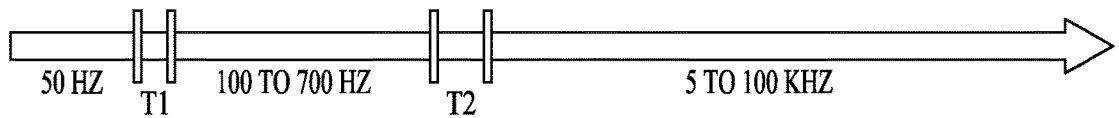

It is noted that FIG. 5A is a simple illustration of frequency ranges, and that these ranges may vary for different applications. FIG. 5B provides another illustration of a response of a neural muscular junction to different stimulation frequencies. FIG. 5B illustrates a transition period T1 between the activation and depletion block ranges. Transition period T1 may depend on the transmitter and the synaptic end-organ, and may range from about 70 to 130 Hz. FIG. 5B also illustrates a transition period T2 between the depletion block and conduction block ranges that may provide a combined depletion and conduction block.

Some characterizations of depletion block, combined depletion and conduction block, and high frequency kHz conduction blocks are provide below. For example, a depletion block has a lower frequency and thus lower power requirements, has a relatively fast block (<100 ms) and a relatively fast recovery (<100 ms over 50% and 10 seconds 100%). For example, a combined depletion and conduction block (e.g. around 1 kHz) may block slow fibers extremely fast due to conduction block, may be initiated with a high kHz frequency and then lowered to keep the block at lower frequencies, may block slower fibers in less than 7 ms, and may have a faster recovery than the higher frequency kHz blocks. For example, a high frequency kHz conduction block is fast (e.g. on: <7 ms an off: <10 ms), but is more energy intensive due to higher frequencies and current requirements.

For example, a kHz conduction block may be observed with a lower boundary of about 1 kHz to 5 kHz rather than the simply illustrated 1 kHz. Additionally, the upper boundary of a depletion block may be about 2 kHz rather than the simply illustrated 1 kHz. Further, the frequencies for which stimulation transitions from depletion to conduction depends on the nerve fibers and end plate. Fast α-fibers have higher conduction and firing rates, so they will not necessarily block at 1 kHz, and slower fibers will block at lower frequencies (e.g. 600 Hz). Thus, there may be a nerve stimulation frequency band within which most fibers can be activated, a depletion block frequency band for which most fibers may be depleted, and a kHz conduction block frequency band for which most fibers have their action potentials blocked. By way of example, the nerve stimulation frequency band may extend up to about 50 Hz, the depletion block frequency band may extend between about 100 Hz to about 700 Hz, and the kHz conduction block frequency band may extend from about 5 kHz to 100 kHz. There may be transition frequencies between the bands, such as a transition between about 50 Hz to about 100 Hz or between about 70 Hz to 130 Hz for example and another transition between about 700 Hz to about 5 kHz. The response of the nerve to the stimulation frequency appears to depend on the transmitter and the synaptic end organ. Thus, different types of fibers may react differently for frequencies within the transition frequencies. By way of example, one frequency may cause an activation or neural stimulation of some fibers, and cause a depletion block in other fibers. The stimulation may be limited to specific fibers by the diameter or origin of the fibers or the location of the electrodes. For example, a frequency of the depletion block stimulation may be found to discriminate between afferent and efferent nerve fibers, or to discriminate between different fibers that emit different types of neurotransmitters. Such a frequency capable of providing both depletion block and activation/stimulation may be found in a transition region, but also may be found in one of the frequency bands such as within the depletion block frequency band.

Although the response to different frequencies may and is expected to change from application to application, the stimulation parameters for delivering a depletion block are expected to be available in current devices at reasonable energy consumption costs. In the study illustrated in the table where stimulation is provided at a pulse width of 300 μs, A-fibers were blocked at 2 mA, 200 Hz while still exciting B fibers that drove heart rate down at 5 mA, 20 Hz.

As illustrated in Table 2, the speed of the depletion block depends on the frequency of the stimulation, where higher frequencies within the range of about 100 Hz to about 1 kHz provide the neurotransmitter block more quickly than the lower frequencies within that range. According to some embodiments, the depletion block may be implemented by a process that initiates the depletion block at a relatively high frequency (e.g. about 200 Hz to 400 Hz) to achieve fast depletion (e.g. about 50 ms or less), and then subsequently lower the frequency of the depletion block stimulation to about 100 Hz to maintain the block. As the lower frequency stimulation delivers fewer pulses, the lower frequency depletion block is more energy efficient than the higher frequency depletion block. If the depletion block was started at about 100 Hz rather than 200 Hz, it would take longer to achieve the depletion block. Based on current observations, it is believed that the depletion block at 100 Hz will take about 5 seconds to 10 seconds. The use of two (or more) stages of frequencies can be used to obtain benefits of each frequency, such as inducing depletion block relatively quickly using a one frequency and then maintaining depletion block relatively efficiently using another frequency.

Various embodiments may use a depletion block at the synaptic junction to provide selective fiber communication. A depletion block may be limited to specific fibers by diameter or origin or location to the electrode. The amplitude of the depletion block pulses can be controlled to be greater than only the stimulation threshold for only some of the nerve fibers. Thus, although all fibers may be with other pulses that causes action potentials to propagate, the pre-synaptic terminal for some of the fibers are quickly depleted from their ability to communicate across the synaptic junction because the frequency of the stimulation causes the depletion block. Various stimulation waveforms may be used including non-sinusoidal or sinusoidal waveforms. Non-sinusoidal waveforms may include rectilinear pulses, charge balanced waveforms that may include biphasic rectangular pulses, quasi-trapezoidal for unidirectional applications, and pulsed triangular. Neural stimulation that elicits nerve traffic and a desired physiological response as part of neural stimulation therapy may be referred to as a low frequency stimulation (e.g. about 20 Hz or within a range of about 0.25 Hz to about 50 Hz); whereas in comparison a depletion frequency may be referred to as high frequency (e.g. about 200 Hz or within a range of about 100 Hz to about 1 kHz). The stimulation at these lower frequencies that is effective in activating nerve fiber(s) to deliver a nerve stimulation therapy may be referred to herein simply as "nerve stimulation" or "neural stimulation;" whereas the stimulation at the higher "depletion" frequencies may be referred to herein simply as a "depletion block stimulation." A "high amplitude, low frequency" (HALF) stimulation signal may exceed a stimulation threshold and thus may be used to recruit both small and big fibers. As such, a HALF signal may be used to obtain the desired effect of the stimulation by capturing all the necessary A sensory and B efferent fibers. A "small amplitude, high frequency" (SAHF) stimulation signal may be set at an amplitude that it only exceeds a stimulation threshold and thus only recruits the bigger fibers with the lower stimulation threshold while leaving the smaller fibers still excitable with the HALF stimulation. The depletion block stimulation cancels the effectiveness of all signals that are evoked at lower frequencies (e.g. 20 Hz) with the same or lower amplitude. SAHF may be used to achieve the neurotransmitter depletion block of the large fibers which are the fibers with relatively low stimulation thresholds but not the smaller fibers which are the fibers with relatively high stimulation thresholds. In some embodiments, the higher frequency depletion block stimulation may be delivered using the same or approximately the same high amplitude as the low frequency stimulation to reduce or modulate the effect of the applied therapy using the low frequency stimulation.

The current amplitude and the pulse width control whether an axon is depolarized, and the frequency of the stimulation controls whether the neurotransmitters are depleted at the nerve ending. The current amplitude and pulse width may be controlled to select only larger fibers for the depletion block. For example, the current amplitude and pulse width may be controlled to deplete the A fibers and not the smaller fibers, or may be controlled with higher amplitudes and/or wider pulse widths to deplete both A and B fibers.

By way of example and not limitation, a full neurotransmitter block for intended fibers may be ensured by acquiring a recruitment curve. The recruitment curve may identify the activation threshold and saturation threshold for the neural target. The recruitment curve may be specific to an individual patient, may illustrate an increase in activity with increasing current amplitude, and may then illustrate a plateau where the activity does not significantly increase with increasing current amplitude. The activation threshold reflects where the nerve activity begins to increase with increasing current amplitude, and the saturation threshold reflects where the nerve activity does not significantly increase in response to further increases in current amplitude. The saturation threshold indicates a threshold where all or almost all of the nerve fibers propagate action potentials. The current amplitude for the depletion block stimulation may be higher than and based on the saturation threshold of the fibers that are intended to be blocked. By way of example, the amplitude of the depletion stimulation signal may be approximately 125% of the saturation threshold of the fibers that are intended to be blocked.

A procedure can be implemented to determine each individual patient's selective fiber stimulation therapy profile, as there may be patient variation or variations resulting from electrode spacing from nerves fibers. The particular procedure will depend on the particular neural target that is stimulated, as the nerve fibers in different neural targets innervate different portions of the body. For example, if a cervical vagus nerve is targeted, the patient's selective fiber stimulation therapy profile may be determined by observing laryngeal vibration as well as blood pressure and heart rate fluctuations. Thus, various embodiments for providing a depletion block may first find an activation threshold and saturation threshold for a neural target. The current amplitude may be selected to be above the saturation threshold of the neural target, and the frequency may be selected for a given application to be high enough (e.g. 200 Hz) to quickly deplete the presynaptic terminal of its ability to communicate across the synaptic cleft to provide an effective depletion block for that application. The procedure may transition the frequency of the stimulation while monitoring the physiological effects to transition between different types of block (e.g. transition between depletion block and kHz conduction block), or to improve efficiency, or to improve time constants (e.g. onset/restoration), or to find a desired frequency and location that both activates some nerve fibers and also provides a depletion block for other nerve fibers.

Some embodiments may ramp up stimulation. Ramping up the stimulation may provide a graded block that may make the stimulation more tolerable. In a neural muscular junction depletion block, for example, the ramped stimulation may reduce the force of the one initial muscle activity at start of stimulation by creating an initial period of graded block. Some embodiments may change the frequency of stimulation signal during the block. Thus, higher frequency stimulations may be used to quickly obtain the block, and then lower frequency stimulation may be used to maintain the block that was previously obtained. For example, an initial frequency (e.g. 260 Hz) may be used to quickly achieve depletion block followed by a second frequency (e.g. 130 Hz) to maintain the depletion block. The frequency of stimulation is related to how long for complete or 90% depletion block. For example, frequencies within the range of about 100 to about 150 Hz provide a 90% depletion block in about 10 to 4 seconds, and frequencies within the range of about 200 to 1000 Hz provides a 90% depletion block less than one second (e.g. on the order of milliseconds). Frequencies greater than 1 kHz start to enter into nerve conduction block.

Figure 6:
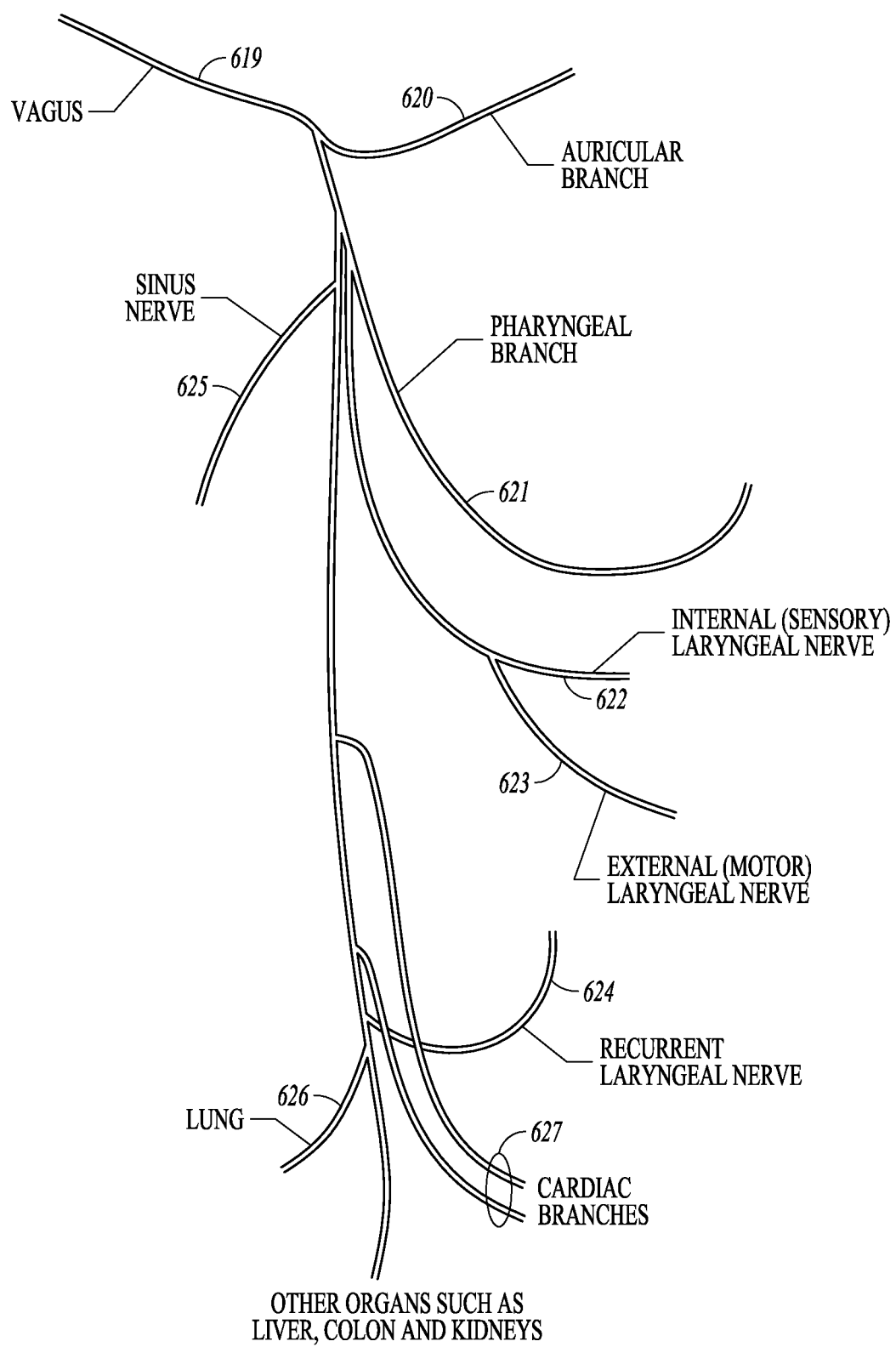
FIG. 6 illustrates some branches from the cervical vagus nerve.

The present subject matter may be used in applications that stimulate the vagus nerve, or in applications that stimulate branches from the vagus nerves (e.g. pulmonary branches from the vagus) or other nerves. The vagus nerve is discussed herein as an example of a complex nerve. The vagus nerve is part of the autonomic nervous system (ANS) which is briefly discussed below. FIG. 6 illustrates some branches from the cervical vagus nerve. The cervical vagus nerve 619 is a combined nerve that separates into a number of branches, including the auricular branch 620 which innervates areas around the ear, the pharyngeal branch 621 that innervates areas around the pharynx, the internal 622 laryngeal nerve, external laryngeal nerve 623 and recurrent laryngeal nerve 624 that innervate areas around the larynx, the sinus nerve branch 625 which innervates the carotid sinus along with branches from the glossopharyngeal nerve, pulmonary branches 626 that innervate the lungs, and cardiac branches 627 that innervate the heart. The vagus nerve continues to innervate other portions of the body including the liver, stomach, intestines, bladder and kidneys.

The ANS regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscles around blood vessels, for example. The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent nerves convey impulses toward a nerve center, and efferent nerves convey impulses away from a nerve center.

Stimulating, as well as inhibiting or blocking, the sympathetic and parasympathetic nervous systems can cause heart rate, blood pressure, respiration, and other physiological responses. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intestine, increases urine secretion, and contracts the wall and relaxes the sphincter of the bladder. Various embodiments of the present subject matter provide a depletion block of parasympathetic fibers that innervate the bronchial muscle, and thus relaxes the bronchial muscle. For example, all fibers (both small and large thresholds) could be blocked in a bronchial tree to achieve a similar effect as RF ablation or denervation. Afferent or efferent fibers may be blocked. The functions associated with the sympathetic and parasympathetic nervous systems are many and can be complexly integrated with each other.

Some embodiments disclosed herein may provide reversible depletion block to targeted nerve regions in the airways to reduce parasympathetic drive and alleviate symptoms of pulmonary disease. The depletion block may be used to reduce the occurrence of AECOPD by reducing parasympathetic input that causes bronchoconstriction and mucus production. Some embodiments may also provide a reversible depletion block to targeted nerve for other treatments, such as to reduce chronic cough and dyspnea for example. Dyspnea, for example, may be reduced by eliminating some of the afferent activity contributing to the Herring Breuer reflex, possibly reducing the occurrence of dynamic hyperinflation.

Temporarily blocking sensory traffic may interrupt the cascade leading to a strong asthmatic response. A small/beginning asthmatic or COPD response might be stopped early with a small dose of nerve block.

Different neurotransmitters may have different frequency thresholds for depletion. This may be used to discriminate between different types of neural targets near the airways. The depletion stimulation may be set to be between a frequency threshold for depleting neurotransmitters in some axons another frequency threshold for depleting neurotransmitters in other axons. The stimulation may cause a depletion block (or a faster depletion block) for the axons that have the lower frequency threshold for their neurotransmitters, but not the axons that have the higher frequency threshold. For example, there may be a neuro-muscular junction block with one set of neurotransmitter(s), and may also provide a neuro-synaptic block for the autonomic ganglia near the end-organ with another set of neurotransmitter(s), and may also provide a sensory block back towards the brain/spinal cord with yet another set of neurotransmitter. Some embodiments adjust the frequency of the depletion block to provide a desired depletion block for some neurotransmitters. The selected frequency that blocks some axons may stimulate activity in other axons.

Applications

FIGS. 7A-7D illustrate, by way of example and not limitation, various systems that may be used to deliver depletion block stimulation to a targeted region. A system may include one or more electrodes configured for use to deliver electrical stimulation to a neural target. In addition to the electrode(s), the system may also include a pulse generation system configured to be operably connected to the electrode to deliver depletion block stimulation through the electrode to alleviate symptoms of pulmonary disease. The pulse generation system and the electrode may be configured to cooperate to capture axons in the neural target, the depletion block stimulation including a series of pulses at a depletion pulse frequency within a range between 100 Hz to 1 kHz. A pulse generation system may be implemented in a number of ways in different system. Each of the examples illustrated in FIGS. 7A-7D include an representation of a pulse generation system ("PGS") configured to deliver depletion block stimulation through the electrode. The term pulse generation system is not intended to be limited to these examples, but rather applies to any system configured to be operably connected to the electrode to deliver depletion block stimulation through the electrode.

Figure 7A:
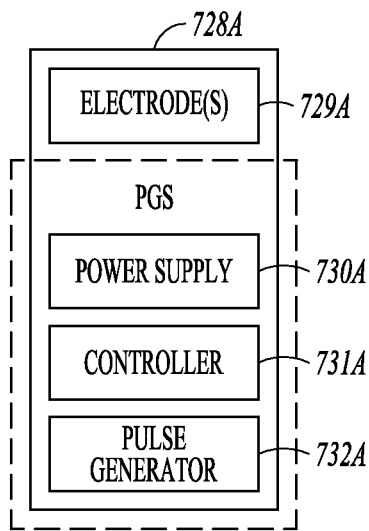
FIGS. 7A-7D illustrate, by way of example and not limitation, various systems that may be used to deliver depletion block stimulation to a targeted region.
Figure 7B:
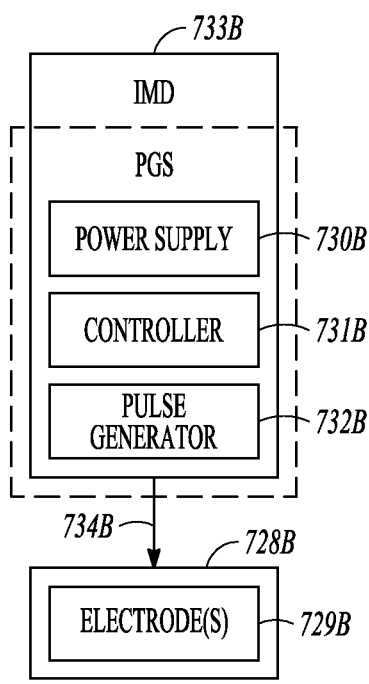
Figure 7C:
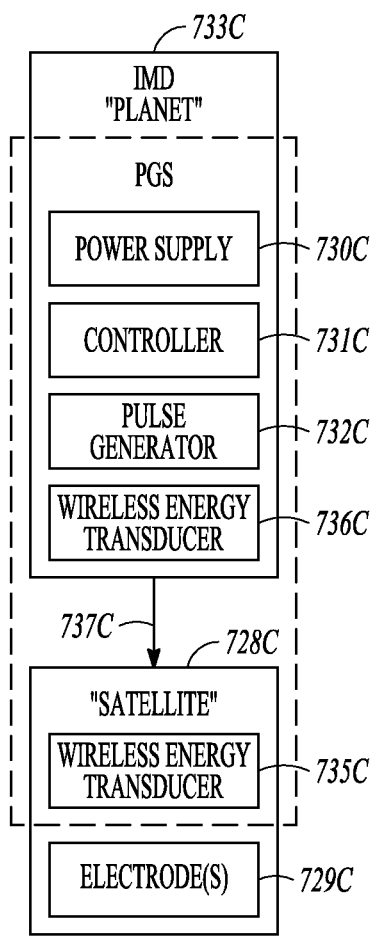
Figure 7D:
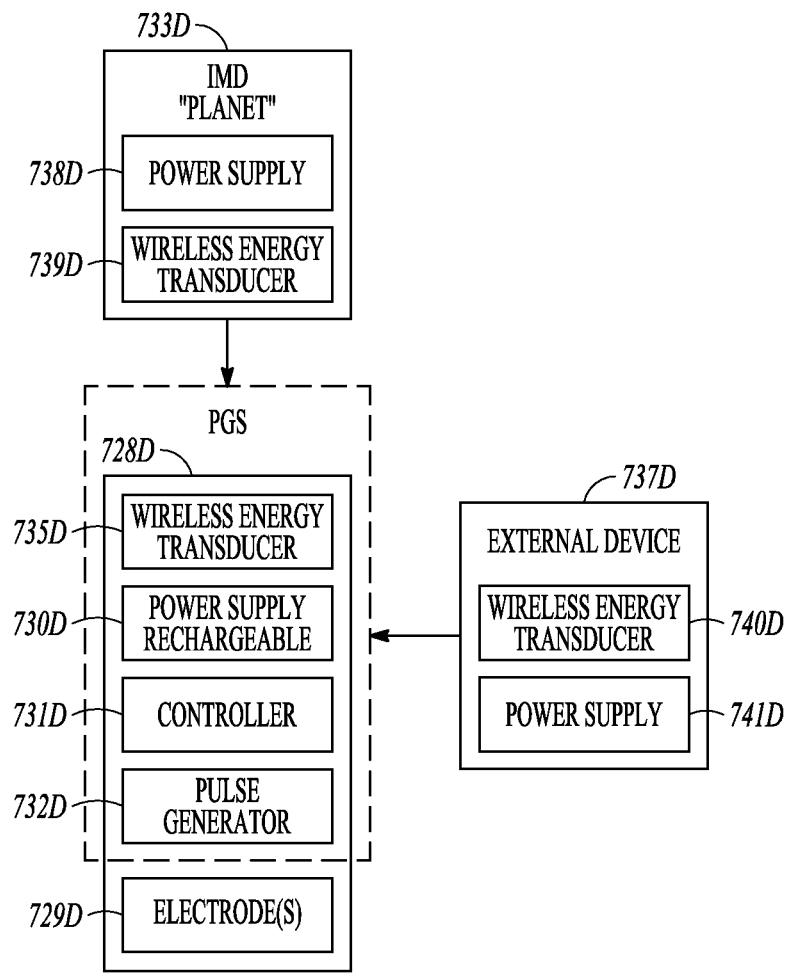

FIG. 7A illustrates an example of a system that includes an electrode device 728A that may be used as a stand-alone device, having one or more 729A, a power supply 730A, a controller 731A, and a pulse generator 732A configured to function together to generate and deliver through the electrode(s). FIG. 7B illustrates an example of a system that includes an implantable medical device (IMD) 733B connected via a lead 734B to an electrode device 728B having one or more electrodes 729B. The IMD 733B may include a power supply 730B, a controller 731B, and a pulse generator 734B configured to function together to generate and deliver electrical stimulation pulses through the lead 734B and electrode(s) 728B. FIG. 7C illustrates an example of a system that includes an IMD 733C functioning as a planet and an electrode device 733D functioning as a satellite. The electrode device 733D may include electrode(s) 728C and a wireless energy transducer 735C configured to convert a wireless signal and convert it into electrical pulses delivered through the electrode(s). The IMD 733C may include a power supply 730C, a controller 731C, a pulse generator 732C, and a wireless energy transducer 736C configured to cooperate together to generate a wireless energy signal 737C that is received and used by the satellite device 728C to generate the electrical stimulation. Examples of a wireless energy signal include, but are not limited to, ultrasound and radiofrequency signals. FIG. 7D illustrates an example of a system that includes an electrode device 728D with electrode(s) 729D, a power supply 730D which may be a rechargeable power supply, a controller 731D and a pulse generator 732D configured to cooperate together to generate and deliver electrical stimulation pulses through the electrode(s) 729D. The electrode device 728D may also include a wireless energy transducer 735D which may be used to recharge the rechargeable power supply 730D. The system may include an IMD 733D that functions as a planet and/or may include an external device 737D. The IMD 733D may include an IMD power supply 738D and an IMD wireless transducer 739D which may be configured to deliver a wireless signal used by the electrode device 728D to recharge the power supply 730D. The external device may include an external device power supply 740D and an external device wireless transducer 741D may be configured to deliver a wireless signal used by the electrode device 728D to recharge the power supply 730D. The IMD and/or the external device may also be configured to program, control or otherwise communicate with the electrode device 728D using the wireless signal.

The external device may include a user interface and may be otherwise configured to allow a human such as the patient, a clinician or other caregiver to initiate a therapy, such as may be desired upon the onset of an AECOPD event. Further, the external device may be configured to provide remote communication (e.g. cellular communication), through which a clinician may remotely communicate with the electrode device 728D. The system may be configured to run until the patient, clinician or other caregiver stops the therapy, or may be configured to run for a programmable period of time. The patient, clinician or other caregiver may reinitiate the therapy if the symptoms of AECOPD event have not subsided.

Some embodiments may include a sensor configured to detect bronchoconstriction or mucus production, or otherwise detect the onset of acute exacerbation or pulmonary disease symptom, such as cough, hyperinflation, and the like. For example, the sensor may be configured to sense a parameter correlated to increased airway resistance. Some embodiments are configured to automatically respond to the detected event by activating the reversible depletion block. The system may be configured to run until the patient, clinician or other caregiver stops the therapy, or may be configured to run for a programmable period of time or may be configured to run until the sensor(s) indicate that the symptoms have subsided. An impedance sensor may be used to sense a reduction in transthoracic impedance that indicates increased bronchoconstriction, airway inflammation, and mucus production. The impedance sensor may provide a measure of impedance as voltage over current, or may provide a measure of the frequency profile of impedance. The sensor may be a pressure sensor implanted in the airways. A detected increase in pressure indicates increased airway resistance attributable to bronchoconstriction, inflammation, and/or mucus production. The sensor may be a pressure sensor implanted in the pleural space. A significant reduction in pleural pressure indicates the patient is trying harder to take in a breath, which also indicative of increased airway resistance attributable to bronchoconstriction, inflammation, and/or mucus production.

The electrode-to-nerve interface may be characterized by a recruitment curve that represents the kind and number of fibers that are activated with a rising current amplitude. This recruitment curve may identify the Activation Threshold (AT) and the Saturation Threshold (ST). The AT describes the current necessary to achieve the first response on the nerve (measured by electro-neuro-gram ENG, and could be confirmed by a voltage signal in an end-organ such as a muscle via electromyogram EMG). The ST, being larger than the AT, defines the current level at which no more increase in nerve response and end-organ response can be measured, translating into the current that provides the recruitment of all nerve fibers of a specific size within the nerve. Stimulation above ST activates all fibers of a specific size within a nerve.

Some embodiments that provide a full or partial depletion block of a nerve may set the stimulation matters by finding a saturation threshold (ST) of nerves driving muscle using force and/or EMG, and the nerves may be depolarized using about a 200 Hz frequency or higher frequency at 100% to 200% of the ST. For a full block, the depletion signal may be kept at 100% to 200% of the ST and at 200 Hz. To save power while maintaining a full block, the depletion signal maybe kept at 100 to 200% of the ST, but the frequency may be reduced to 100 Hz, by way of example. For a partial block, the depletion signal may continue to be delivered at 200 Hz but the intensity of the stimulation may be reduced to 10 to 90% of ST. The intensity of the stimulation for the partial depletion block still captures some fibers, and thus is greater than AT. To save power while maintaining the partial block, the frequency may be reduced (e.g. from 200 Hz to 100 Hz) while keeping the intensity of the stimulation at 10 to 90% of ST.

Airway Electrode Devices

Figure 8:
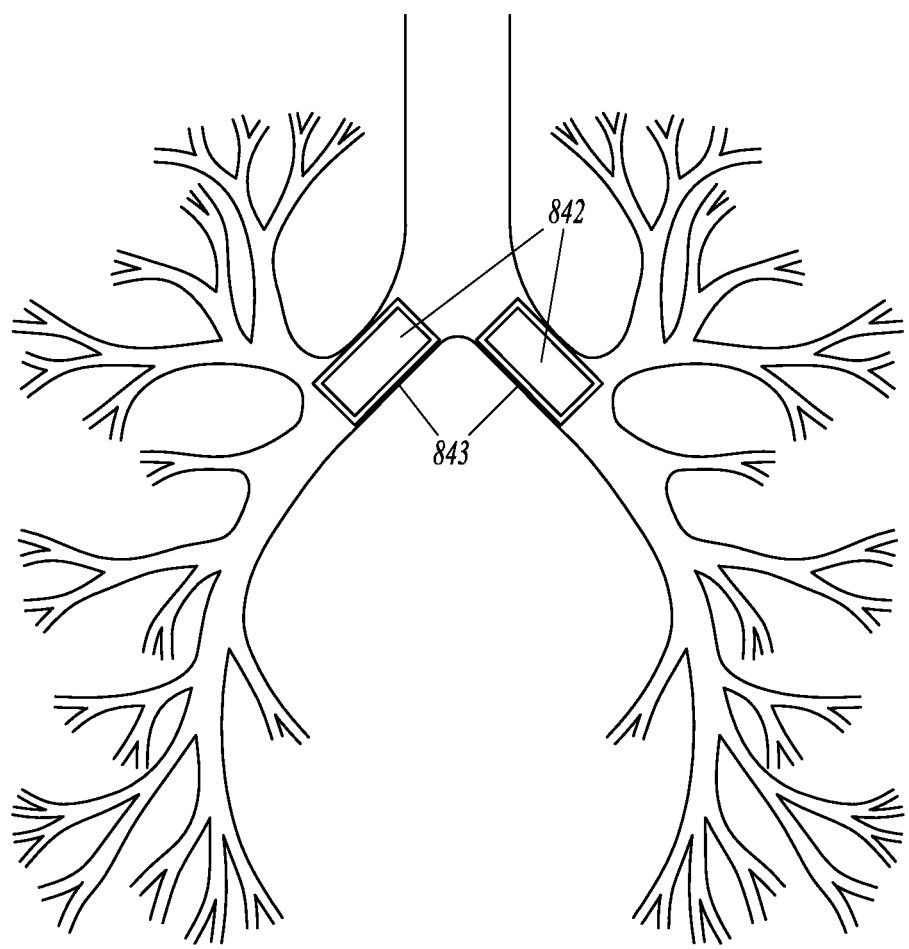
FIG. 8 illustrates an example of stent-like electrode devices configured to be implanted in an airway.

FIG. 8 illustrates an example of stent-like electrode devices configured to be implanted in an airway. These airway electrode(s) 842 may be used to alleviate symptoms of pulmonary disease. The airway device may include a stent structure configured to be expanded within the airway to contact an interior surface of the airway structure. Various types of expandable electrodes, which may but need not have the shape of a stent, may be implanted in an airway. Another example of an expandable device includes a balloon with electrodes. The expandable electrodes may contact the inner lumen of the airway or pierce into or through the inner lumen of the airway. The electrode(s) may be configured to be implanted permanently or temporarily allowing for removal. For example, a temporarily implanted electrode may be used to test the efficacy of a targeted depletion block for a patient which may be beneficial before a device is permanently implanted to provide the depletion block or before nerves in the targeted region are ablated. For example, the implantable electrode(s) include a stent electrode configured to be deployed, either temporarily or permanently, in the airways. The neural target may be located proximate to the 1st generation bronchi which may also be referred to as a mainstem bronchi 843, along which pulmonary branches of the vagus nerve traverses. The neural target may be parasympathetic fibers from the vagus nerve proximate to the trachea, or the neural target may be proximate to later generation bronchi, such as one of generations 2-7 where branches of the vagus nerve also traverse. Some branches appear to enter slightly distal to the mainstem ($1^{st}$ generation) bronchi. The stent electrode may be powered by any of a number of pulse generator sources. For example, the electrode may be powered by a rechargeable power source operably connected to the electrode and implanted within the airway with the electrode. The stent electrode may be manufactured using a common stent material, such as Nitinol, Stainless Steel, Elgiloy, and the like. The expandable electrode may be configured to contact the inner lumen of the airway, or pierce through the inner lumen of the airway some distance (e.g. <2 mm) to achieve greater proximity to the target nerve(s).

Some system embodiments may be configured to deliver unipolar stimulation using electrode(s) implanted in the airway, where another electrode outside of the airway provides a return electrode. Some system embodiments may be configured to deliver bipolar stimulation using electrodes implanted in the airway. Some system embodiments may be configured to deliver stimulation using a multipolar device implanted in the airway. A stent-like device may be used to deliver unipolar, bipolar or multipolar stimulation, and thus may be configured with one electrode, two electrodes or more electrodes.

The airway electrode(s) may be implemented in a temporary device, intended to be implanted days, weeks, or months as a 'trial' to determine efficacy of nerve block/ denervation prior to the implant of a permanent device or irreversible denervation therapy. The airway electrode(s) may be implemented in a permanent device, intended to be implanted for years. The device may be configured to provide 'on demand' nerve block, activated by the user when needed to alleviate bronchoconstriction, mucus production, dyspnea, or other COPD symptoms. The airway electrode(s) may be implemented in a permanent device, intended to be implanted for years, that is configured to provide constant or intermittent nerve block. The device may be configured with other devices and/or sensors to provide input to the device to initiate therapy during times when the lung/patient is experiencing an exacerbation, elevated vagal tone, airway resistance due to bronchoconstriction and/or mucus production, coughing, hyperventilation, or dyspnea.

Figure 9:
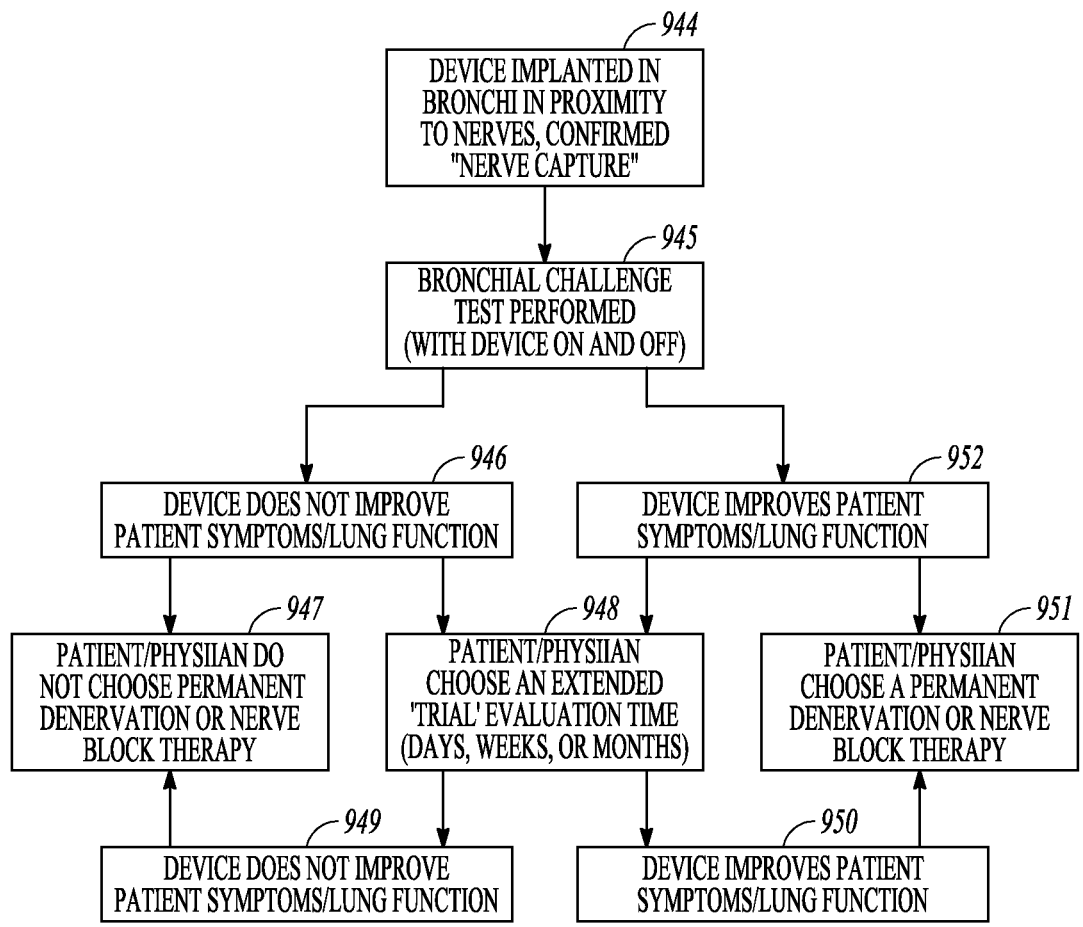
FIG. 9 illustrates an example of a flow chart for temporarily using the device as a trial device.

FIG. 9 illustrates an example of a flow chart for temporarily using the device as a trial device. At 944, the device may be implanted in bronchi proximate to the nerves to be captured, the nerve capture may be confirmed by observing a response to the stimulation. A bronchial challenge test may be performed at 945 both with the device is turned on to deliver the depletion block and then turned off. The referenced bronchial challenge test may be one in which a chemical that stimulates autonomic activity is used in attempt to promote bronchoconstriction, e.g. a nebulized histamine challenge test through an inhaler. Respiratory parameters and symptoms can be monitored pre- and post-challenge and pre- and post-therapy. Alternatively, the challenge test need not be performed, but rather the respiratory parameters (lung function) and symptoms simply be monitored pre- and post-therapy. Some embodiments may trigger a bronchial event (either external via antihistamine or other mechanism, or some device-based trigger or stimulation), initiate the therapy (manual or automatic), and determine of effectiveness of therapy (manual or automatic). Some embodiments may trigger a bronchial event, the device detects the event, and alerts or records or delivers a therapy, and the device delivers therapy and determines an effectiveness of therapy. Some embodiments may trigger a bronchial event, the device may detect the event, and deliver a therapy. In some embodiments, the patient may trigger the therapy. Some embodiments may deliver the therapy to a patient present with symptoms, and determine the effectiveness of the therapy. Some embodiments may individualize sensing (i.e. change automatic gain control (AGC)/sensitivity/refractory based on real-time streaming of sensors) and/or individualize detection algorithm based on patients disease/ symptoms/breathing patterns (normal and symptomatic). The device may be placed into a mode to monitor for bronchial event, and trigger a therapy or alert upon ambulatory detection of event.

The patient symptoms are observed during both the ON and OFF times. If the depletion block during the ON times does not improve patient symptoms/lung function at 946, then the patient and/or physician may choose not to proceed with a permanent denervation therapy or a nerve block therapy at 947, or the patient and/or physician may choose to extend the trial evaluation time at 948. If the extended trial still does not improve patient symptoms/lung function at 949, the patient and/or physician may choose not to proceed with a permanent denervation therapy or a nerve block therapy at 947. However, if the extended trial is found to improve patient symptoms/lung function at 950, then the patient and/or physician may choose to proceed with a permanent denervation therapy or a nerve block therapy at 951. If the bronchial challenge performed at 945 results in improved patient symptoms/lung function at 952, the patient and/or physician may choose to proceed with a permanent denervation therapy or a nerve block therapy at 951, or may choose an extended trial evaluation time at 948 to confirm the efficacy of the depletion block for alleviating the patient symptoms/lung function.

Figure 10:
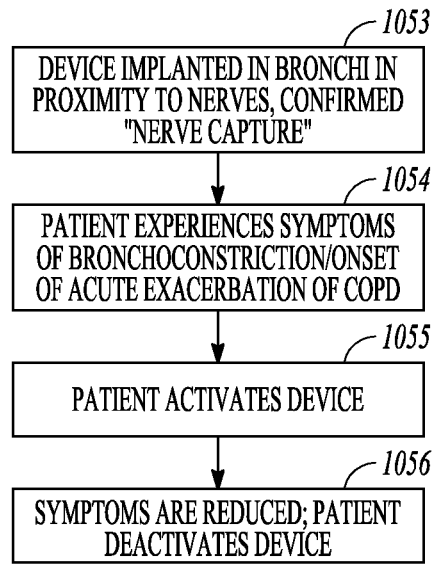
FIG. 10 illustrates an example of a flow chart for a permanent device that is configured to provide on-demand therapy, in response to a human-initiated command from a patient or clinician or other caregiver, such as may be desired at the onset of an AECOPD event.

FIG. 10 illustrates an example of a flow chart for a permanent device that is configured to provide on-demand therapy, in response to a human-initiated command from a patient or clinician or other caregiver, such as may be desired at the onset of an AECOPD event. The command may be delivered when the patient is within or outside of a clinical setting. At 1053 the device may be implanted in bronchi proximate to the nerves to be captured, the nerve capture may be confirmed by observing a response to the stimulation. At 1054 the patient experiences symptoms of bronchoconstriction, mucus production or an onset of AECOPD. The patient (or clinician/physician or other caregiver) may activate the device at 1055 to alleviate the symptoms. After the symptoms have been reduced, the device may be deactivated at 1056.

Figure 11:
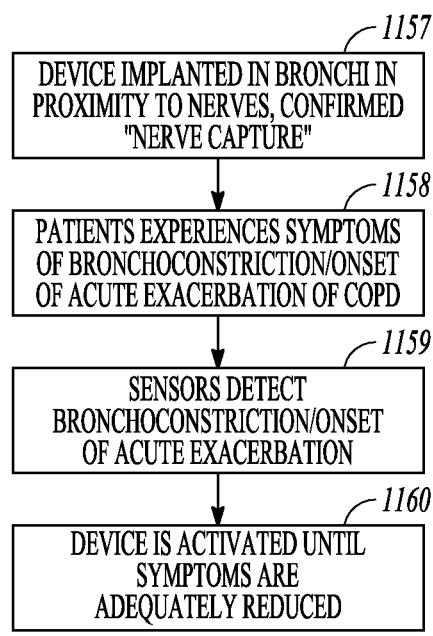
FIG. 11 illustrates an example of a flow chart for a permanent device that is configured to detect an AECOPD event.

FIG. 11 illustrates an example of a flow chart for a permanent device that is configured to detect an AECOPD event. At 1157 the device may be implanted in bronchi proximate to the nerves to be captured, the nerve capture may be confirmed by observing a response to the stimulation. At 1158 the patient experiences symptoms of bronchoconstriction, mucus production or an onset of AECOPD. Sensor(s) may be used to detect symptoms of bronchoconstriction, mucus production or an onset of AECOPD. The device may be automatically activated until the sensor(s) indicate the symptoms are adequately reduced 1160.

FIGS. 12-18 illustrate, by way of example and not limitation, some airway electrode embodiments. Some electrodes may have pacing surfaces that are relatively smooth. Some electrodes may have protrusions that penetrate some distance into the airway wall for improved proximity to the nerve and/or improved 'fixation' in the airway (to prevent migration of the electrode with cough, etc.). Some electrodes may have a non-penetrating surface texture that may improve fixation. The protrusions may be "spikes" or "bumps". The protrusions may be configured to provide a more definite surface connection, and may offer more neural selectivity. For example, spikes pierce into the bronchi and get the electrode tips closer to the other side of the bronchi. Thus, the stimulation or block waveforms may be applied closer to the nerves as the nerves are located on the outside of the bronchi. Thus, the protrusions may both bring the electrodes into closer proximity to the nerves and improve the anchoring of the electrode by penetrating some or all layers of the bronchi. These protrusions (e.g. spikes) may engage the surface after the device is expanded. The expandable device may be similar to a stent. The protrusions may be on a ring, and pushed outward into engagement with the bronchi by an inflatable device (e.g. balloon) during the implantation procedure.

Figure 12:
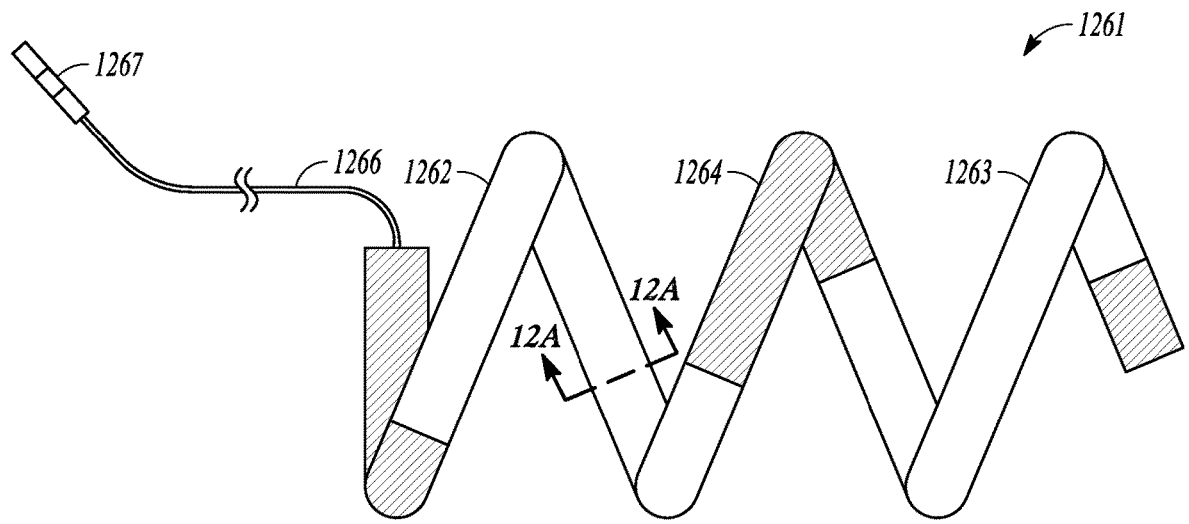
FIGS. 12-18 illustrate, by way of example and not limitation, some airway electrode embodiments.
Figure 12A:
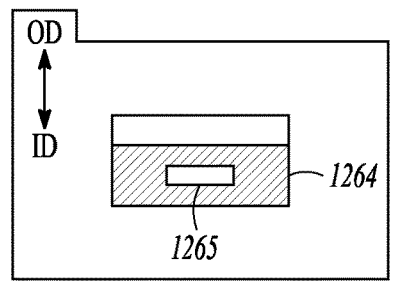

FIGS. 12 and 12A illustrate, by way of an example, an airway electrode device 1261 with helical shape and with a first electrode 1262 and a second electrode 1263. The device may be fabricated from an insulative material 1264, with an electrically active surface that forms the first electrode and that forms a second electrode separated from the first by the insulative material 1264. The insulative material beneath the first electrode may include a conductor 1265 for the second electrode. One end of the airway electrode device may include connectors 1266 for electrically connecting the electrodes to a power source. In some embodiments, the power source 1267 may be implanted within the airway with the airway electrode device. In some embodiments, the connectors may be connected to an antenna configured to receive a wireless signal.

Figure 13:
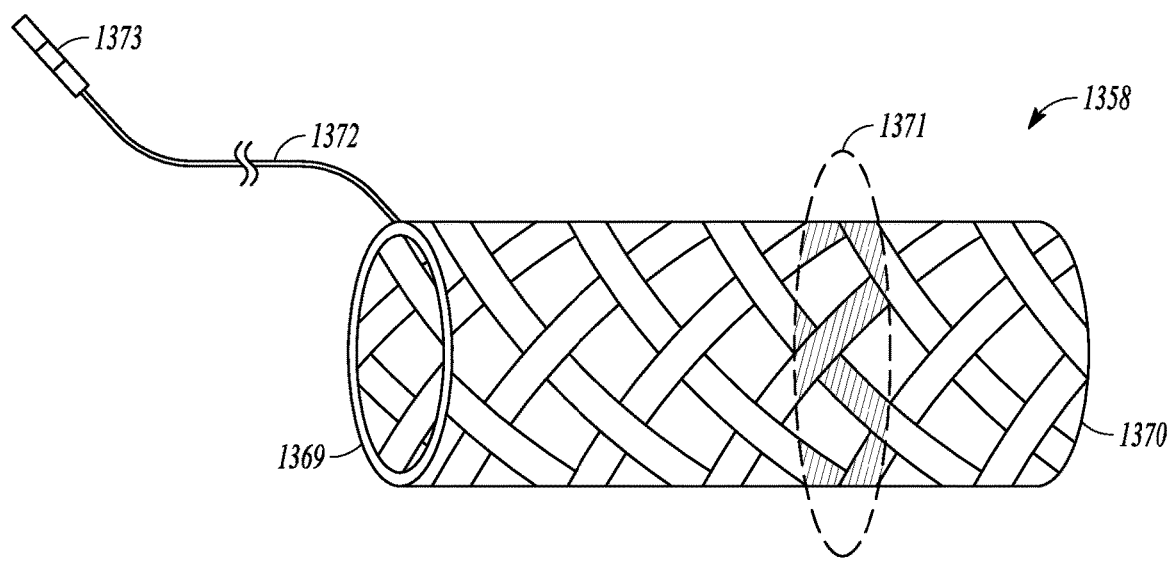

FIG. 13 illustrates, by way of an example, an airway electrode device 1368 with a patterned, stent-like shape. The device 1368 may be formed with one portion of the stent-like electrode to as a first electrode 1369, and a second portion of the stent-like electrode to function as a second electrode 1370. The device 1368 may be used to deliver bipolar stimulation using the electrodes 1369 and 1370. The first and second electrodes 1369 and 1370 may be separated by an insulative material 1371. The device may include connectors 1372 configured to connect the electrodes 1369 and 1370 to a power source 1373. In some embodiments, the power source 1373 may be implanted within the airway with the airway electrode device. In some embodiments, the connectors may be connected to an antenna configured to receive a wireless signal.

Figure 14:
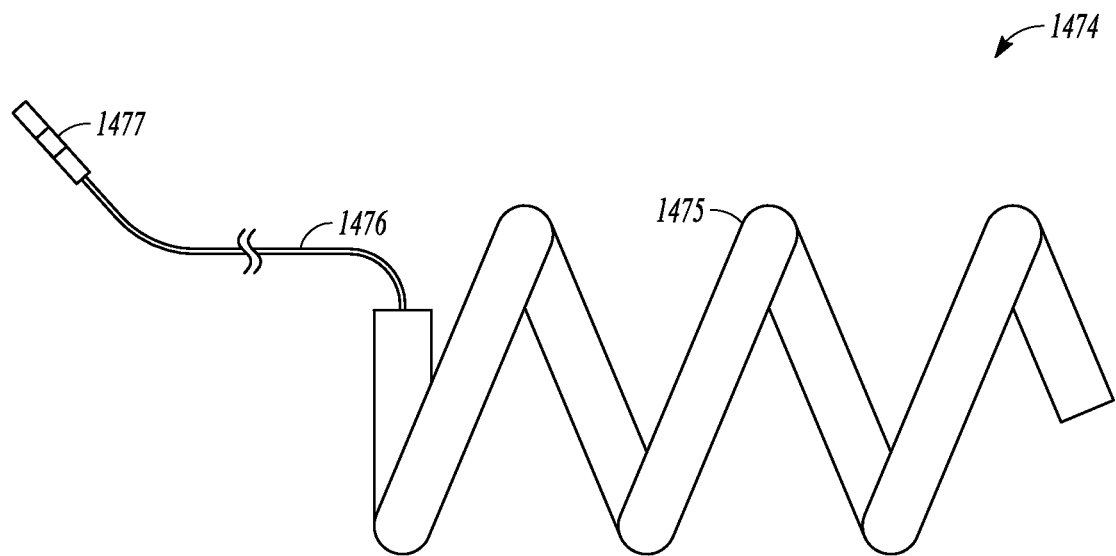

FIG. 14 illustrates, by way of an example, an airway electrode device 1474 with helical shape and with a single electrode 1475 on a surface of the device. The device 1474 may be used to deliver unipolar stimulation using the electrode 1475 in the airway. One end of the airway electrode device may include a connector 1476 for electrically connecting the electrode to a power source. In some embodiments, the power source 1477 may be implanted within the airway with the airway electrode device. In some embodiments, the connector may be connected to an antenna configured to receive a wireless signal.

Figure 15:
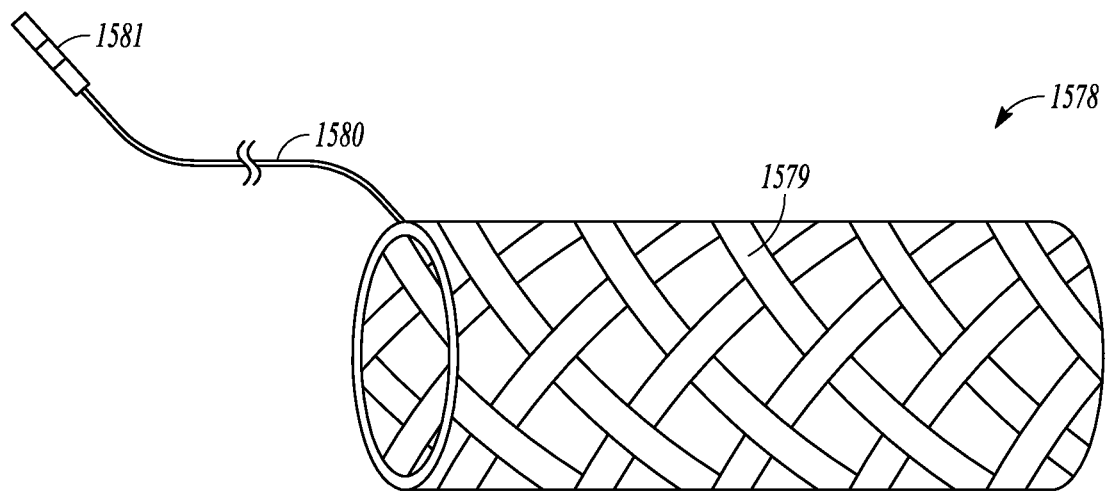

FIG. 15 illustrates, by way of an example, an airway electrode device 1578 with a patterned, stent-like shape. The device 1578 may be formed with a single electrode 1579. The device 1578 may be used to deliver unipolar stimulation using the electrode 1579 in the airway. One end of the airway electrode device may include a connector 1580 for electrically connecting the electrode to a power source. In some embodiments, the power source 1581 may be implanted within the airway with the airway electrode device. In some embodiments, the connector may be connected to an antenna configured to receive a wireless signal.

Figure 16:
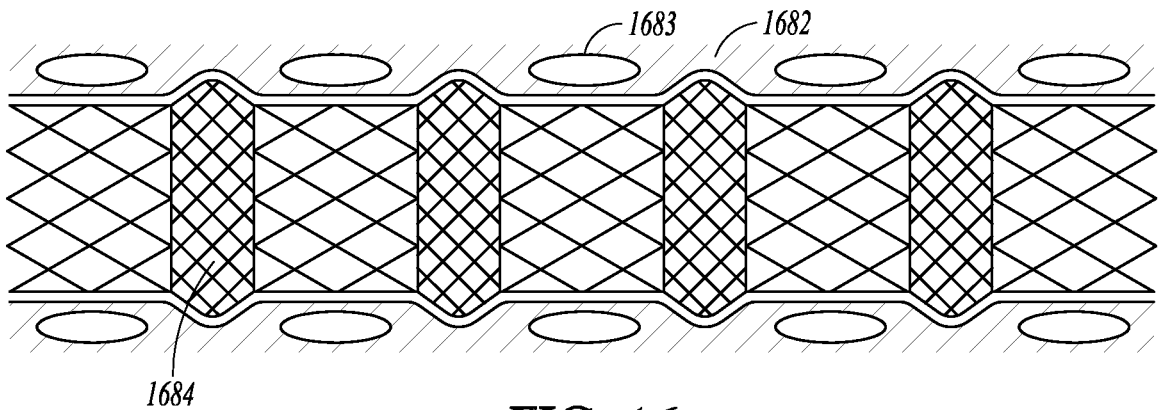
Figure 17:
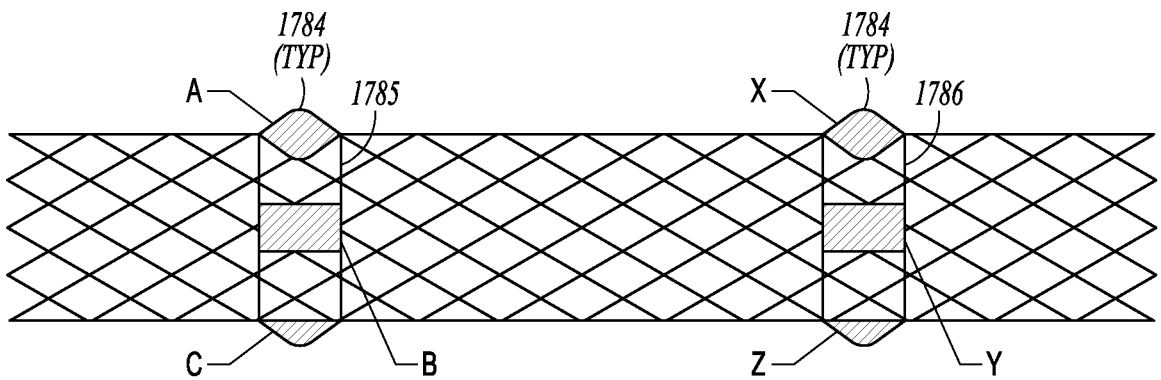
Figure 18:
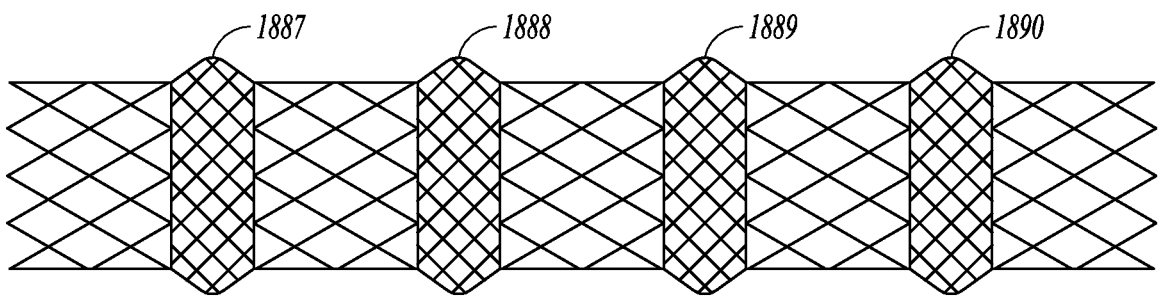

FIGS. 16-18 illustrate, by way of example and not limitation, some embodiments of airway electrodes configured to be positioned between cartilage rings within an airway wall. FIG. 16 illustrates an airway wall 1682 and cartilage rings 1683 therein. The electrodes 1684 may be annular in shape, and sized to fit in between the cartilage rings 1683. FIG. 17 illustrates more than one discrete electrode 1784 on each of the annular-shaped electrode devices 1785 and 1786 designed to be seated between the cartilage rings. The electrodes may be, but need not be, evenly-spaced about the circumference of the devices By way of example and not limitation, each device may include three electrodes. The system may be configured to change stimulation vectors between any electrode A, B, C on device 1784 and any electrode X, Y, Z, such the at the vector may be AX, AY, AZ, BX, BY, BZ, CX, CY, or CZ. The vectors maybe reversed. Further, multipolar stimulation may be delivered using more than two electrodes. FIG. 18 illustrates one electrode on each of the annular-shaped electrode devices 1887, 1888, 1889 and 1890. These devices are designed to seat between cartilage rings. The system may be configured to deliver stimulation using any one or any combination of the devices. Some embodiments of the airway electrodes may be designed with piercing elements on the electrode surface to improve the proximity of pacing surface to target nerves and also improve fixation within the airway.

The stent material itself may serve as the electrode surface, or thin-film electrodes may be attached to the outer diameter of the stent material to serve the pacing function, in which case the stent materials may include elastic polymers. The stent electrode may include electrodes that pierce through the epithelium and into/through the airway wall to achieve closer proximity to the nerves and/or nerve trunks. Furthermore, the electrode may not only be used to stimulate, but may also be used to sense physiological parameters. Insulative materials in the devices may include ETFE, PTFE, Silicone, PU, or any of a number of other common long-term implantable insulative materials. For any embodiment, the insulated portions of electrode may be conformal—in other words, the insulation could coat the entire surface of the wire, only being removed in regions where the electrode surface is intended to be at the outside of the device). Alternatively, an insulation 'sheath' over the surface of the stent structure is possible, again with the insulation being removed in regions where the electrode surface is intended to be. It is possible to pattern the insulation in axial and radial directions. Multiple are possible to enable stimulation in different radial quadrants, in addition to axial locations. This may be useful to avoid sensitive areas of the bronchi such as adjacent to the heart, etc. It is possible that different pacing waveforms/frequencies be used between different electrode pairs.

Neurostimulation Leads Adjacent to or Wrapped Around Airway

Some embodiments stimulate target nerve regions in the bronchi by positioning a lead within or adjacent to the airway. For example, the lead may wrap circumferentially around the bronchi in the 1st generation region, or may lie along the outside of the airway in close vicinity to the target nerves. The pulmonary branch of the vagus nerve traverses along the first generation bronchi. Some embodiments may position the lead in or around the trachea. Some embodiments may position the lead in or around later generation bronchi.

Figure 19:
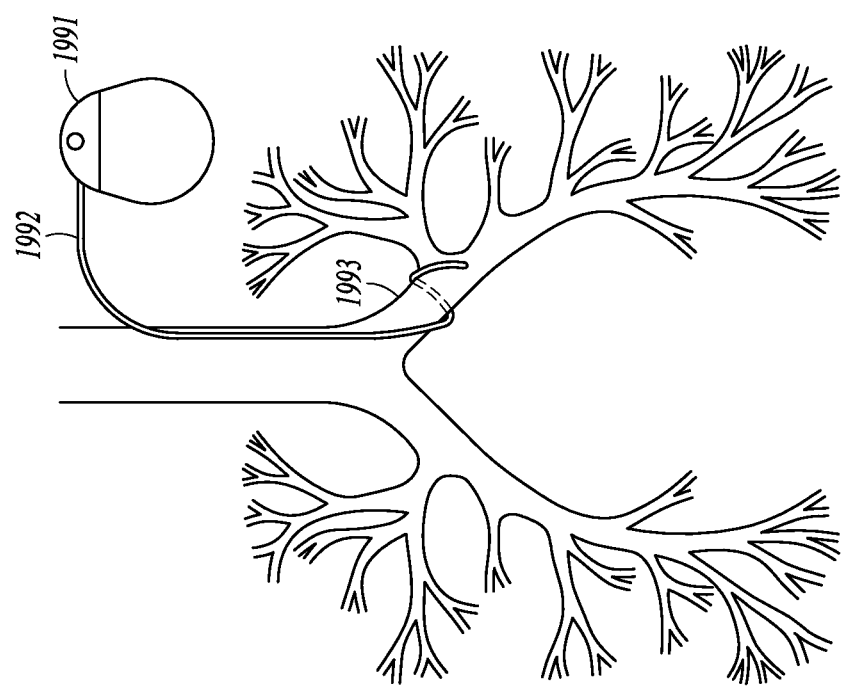
FIG. 19 illustrates an example of a system with an IMD and a neurostimulation lead configured to wrap around bronchus, allowing the electrodes on the lead to be operably paced to stimulate the targeted neural region.

FIG. 19 illustrates an example of a system with an IMD 1991 and a neurostimulation lead 1992 configured to wrap around bronchus 1993, allowing the electrodes on the lead to be operably paced to stimulate the targeted neural region. The distal portion of the lead may be considered to function as an electrode device illustrated in FIGS. 7A-7D. In an embodiment, the neurostimulation lead may be configured to be placed alongside of a bronchus proximate to the targeted neural region, allowing the electrodes on the lead to be operably place to stimulate the targeted neural region. In an example, the lead 1992 may be advanced along the trachea to position the stimulation electrodes by first generation bronchi, and the lead may be connected to the 1991 IMD implanted above the lungs.

The neurostimulation lead 1993, 2093 may include one or more electrodes, allowing the system to deliver unipolar or bipolar stimulation. Some embodiments may use a multipolar lead design, allowing for "electronic repositioning" to adjust stimulation vectors. The lead may be manufactured out of common materials used in implantable cardiac or neurostimulation leads and catheters today, including insulative materials such as ETFE, PTFE, Silicone, PU, etc. and conductors such as MP35N, stainless steel, Pt—Ir, Stainless Steel, Nitinol, Elgiloy, etc. The lead may be fabricated with a shape-memory material to hold a desired shape (e.g. spiral, loop, lasso, etc.) for the application. For example polymers may be thermoformed or metals may be formed into the shape. Superelastic materials such as Nitinol are able to hold their shape very well. The lead may be delivered with a number of delivery tools, including a bronchoscope, guidewire, or steerable catheter, for example, using devices and techniques known in the art for other applications.

Figure 20:
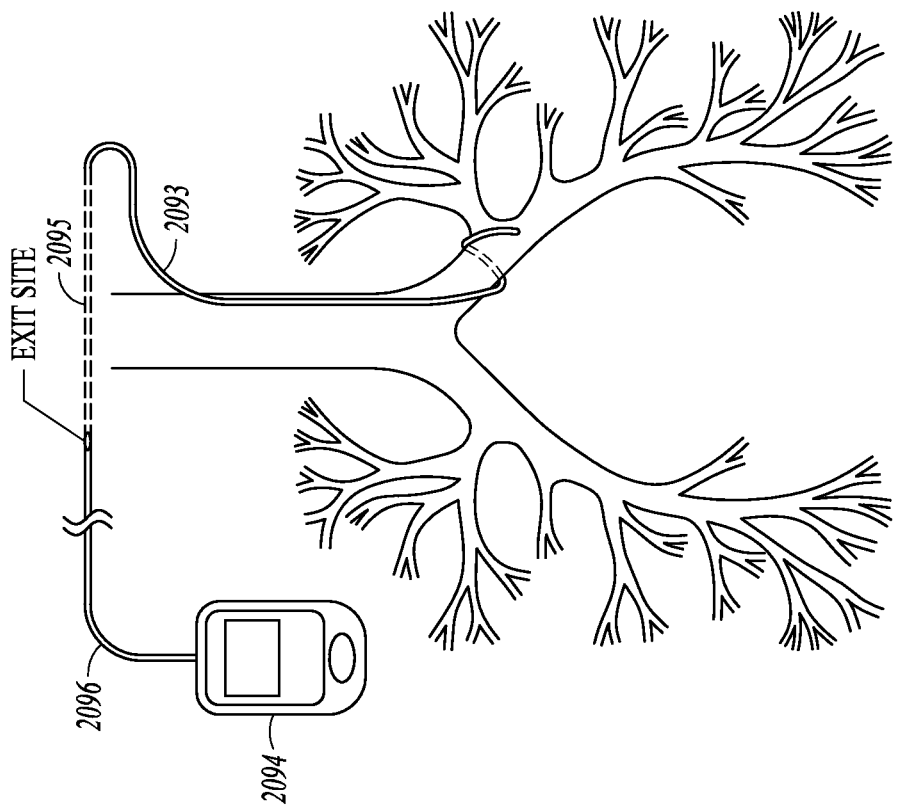
FIG. 20 illustrates an example of a system with an external device and a neural stimulation lead similar to the lead of FIG. 19.

Various embodiments of the present subject matter may be implanted in a "staged implant." FIG. 20 illustrates an example of a system with an external device 2094 and a neural stimulation lead 2093 similar to the lead 1993 of FIG. 19. The system may be beneficial for performing a trial depletion block before providing a permanent block. A permanent lead is still implanted, but a lead extension 2095 is tunneled across the body, thus reducing the infection risk to the permanently implanted lead, to another location where it percutaneously exits the skin and allows a temporary (external) stimulation device 2094 to be attached using an external cable 2096. The patient can then try out the device with the external stimulator for a relatively short period of time such as a few weeks or months. If the trial is successful, the extension lead 2095 may be removed leaving the neural stimulation lead 2093, and an IMD 1991 of FIG. 19 may be connected to the neural stimulation lead 2093. If the trial is not successful, the lead 2093 may be explanted or 'capped' and abandoned without connection to a stimulator.

Figure 21:
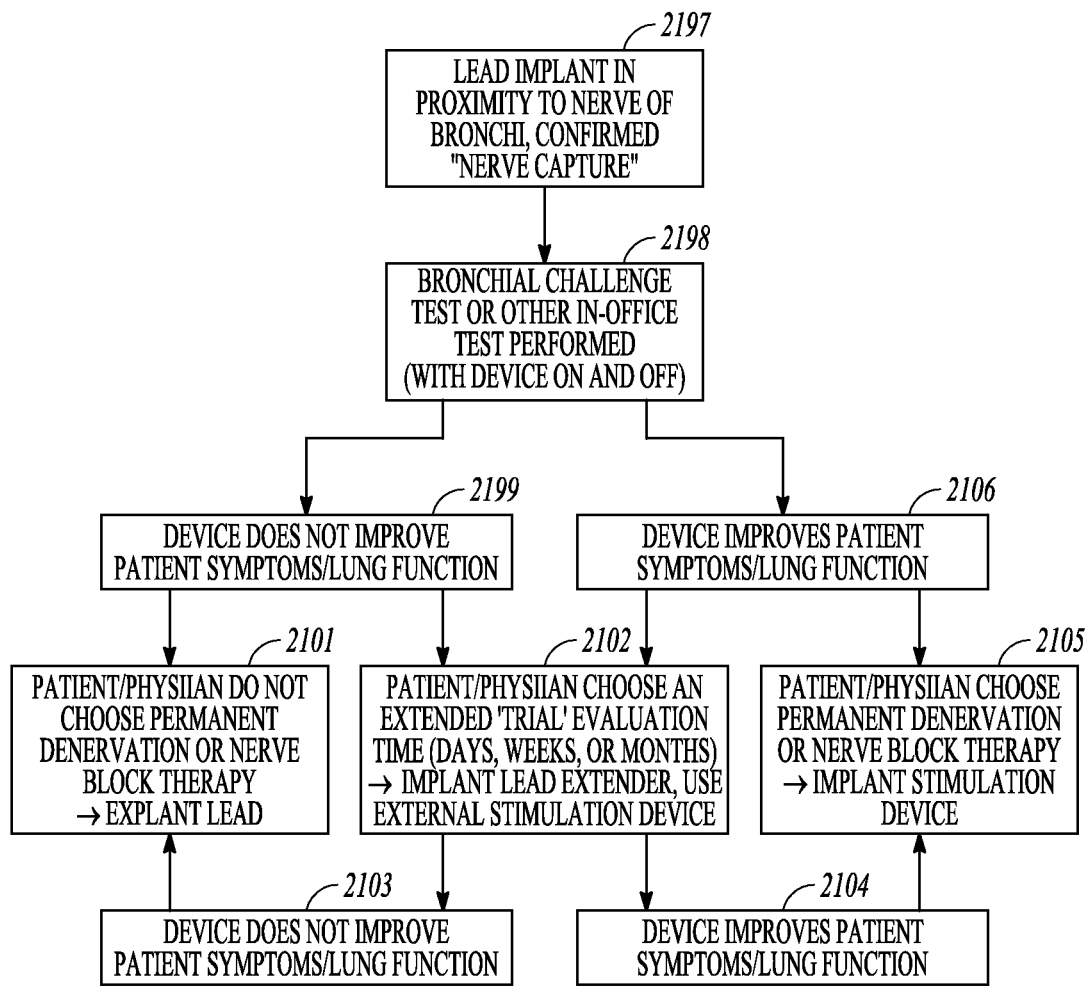
FIG. 21 illustrates an example of a flow chart for using the permanent lead in a staged implant procedure.

FIG. 21 illustrates an example of a flow chart for using the permanent lead in a staged implant procedure. At 2197, the device may be implanted in proximity to nerves of bronchi, and the nerve capture may be confirmed by observing a response to the stimulation. A bronchial challenge test or other in-office test may be performed at 2198 with the device is turned on to deliver the depletion block and then turned off. The challenge test may involve the inhalation of a nebulized histamine, for example. The patient symptoms are observed during both the ON and OFF times. If the depletion block during the ON times does not improve patient symptoms/lung function at 2199, then the patient and/or physician may choose not to proceed with a permanent denervation therapy or a nerve block therapy at 2101 and the lead may be explanted, or the patient and/or physician may choose to extend the trial evaluation time at 2102. A lead extension may be implanted for use with a temporary external device. If the extended trial still does not improve patient symptoms/lung function at 2103, the patient and/or physician may choose not to proceed with a permanent denervation therapy or a nerve block therapy at 2101 and the lead may be explanted. However, if the extended trial is found to improve patient symptoms/lung function at 2104, then the patient and/or physician may choose to proceed with a permanent denervation therapy or a nerve block therapy at 2105. If the bronchial challenge performed at 2198 results in improved patient symptoms/lung function at 2106, the patient and/or physician may choose to proceed with a permanent denervation therapy or a nerve block therapy at 2105, or may choose an extended trial evaluation time at 2102 to confirm the efficacy of the depletion block for alleviating the patient symptoms/lung function.

A lead could be implanted on the right branch, left branch, or both branches. Either full or partial neuromuscular junction block could be achieved, depending upon the desire, to allow more or less afferent/efferent vagal activity in the lungs. The lead configurations and location of deployment in disclosed herein may be applicable to other forms of reversible nerve block as well (i.e. other pacing frequencies).

A benefit of implantation to stimulate the pulmonary vagus trunk (opposed to the cervical area) is that it may have less risk of it adversely affecting other organs, and thus the depletion block may be delivered continuously or near continuously. However, there may be cases where one would choose to have it only active intermittently, on-demand, etc. The device could be configured with a sensor (or sensors) to detect bronchoconstriction and mucus production, or otherwise the onset of AECOPD event (e.g. cough, hyperinflation, etc.) or other pulmonary issue (e.g. chronic cough). The sensor(s) may be used to automatically activate the reversible depletion block therapy when needed. In some embodiments the reversible depletion block therapy may be activated by the patient or a clinician or other caregiver upon the onset of an AECOPD event. The sensor(s) may be implanted with a structure in or near bronchi which is used to provide the depletion block stimulation.

A multipolar lead could be shaped in a zig-zag, spiral, or other form around the bronchus to improve chances of crossing over or coming in close vicinity with target nerve. This design may be fixated passively (no screw-in helix) in close vicinity to the nerve. Multiple electrodes may enable electronic repositioning to choose the best vector to achieve the neuromuscular junction block of nerves in and around the bronchi. The lead may be delivered within an airway using a bronchoscope, or may be delivered from outside an airway.

Figure 22:
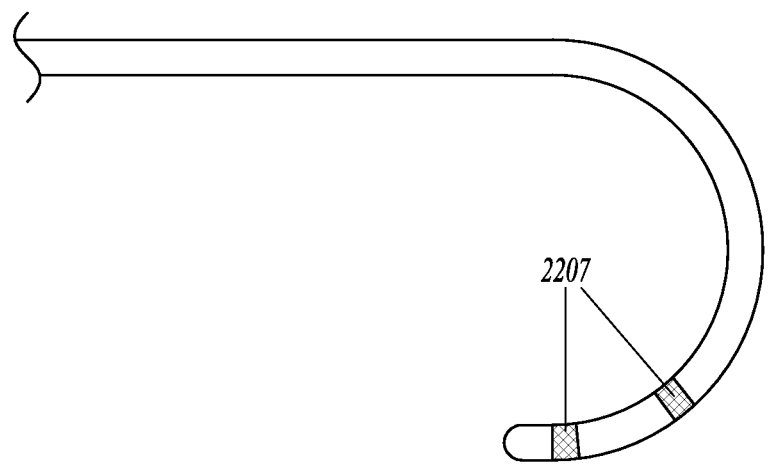
FIGS. 22-24 illustrate some examples of some shapes of neurostimulation leads.
Figure 23:
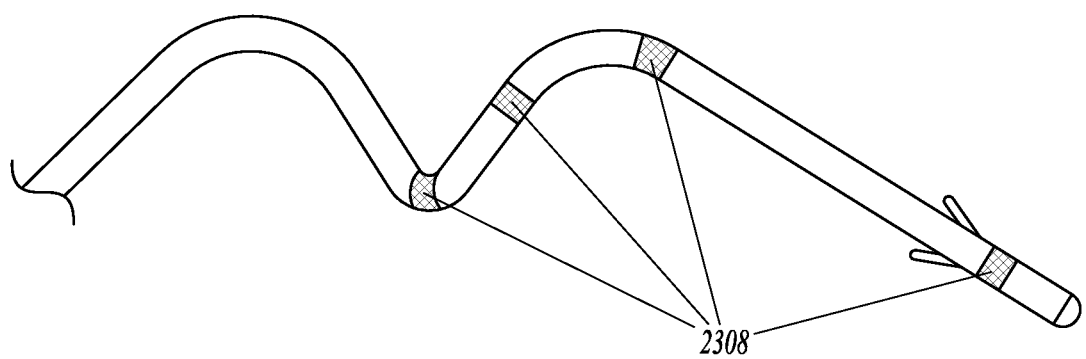
Figure 24:
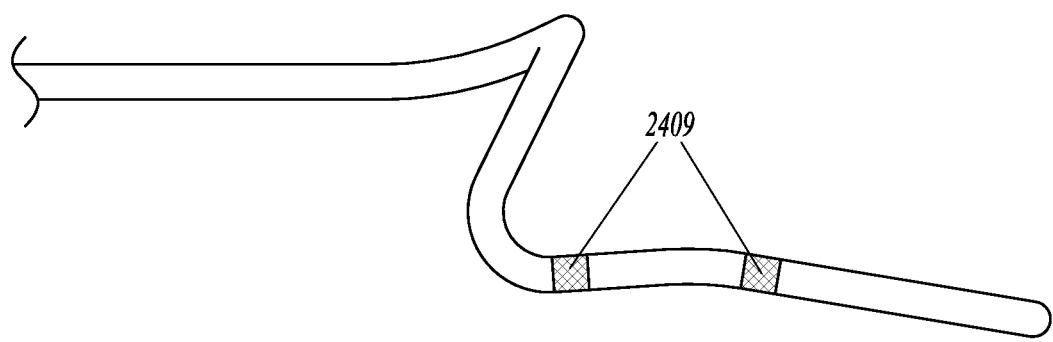

FIGS. 22-24 illustrates some examples of some shapes of neurostimulation leads. For example, FIG. 22 illustrates a bipolar lead with a single curve configured to curve around an airway with the electrodes 2207 at or near the distal end of the lead. FIG. 23 illustrates a multipolar helical lead with more than one wrap with electrodes 2308 around the helical portion for positioning around at least a portion of the airway wrap. FIG. 24 illustrates a bipolar lead with a single wrap and the electrodes 2409 positioned distal to the single wrap for positioning along the airway.

Figure 25:
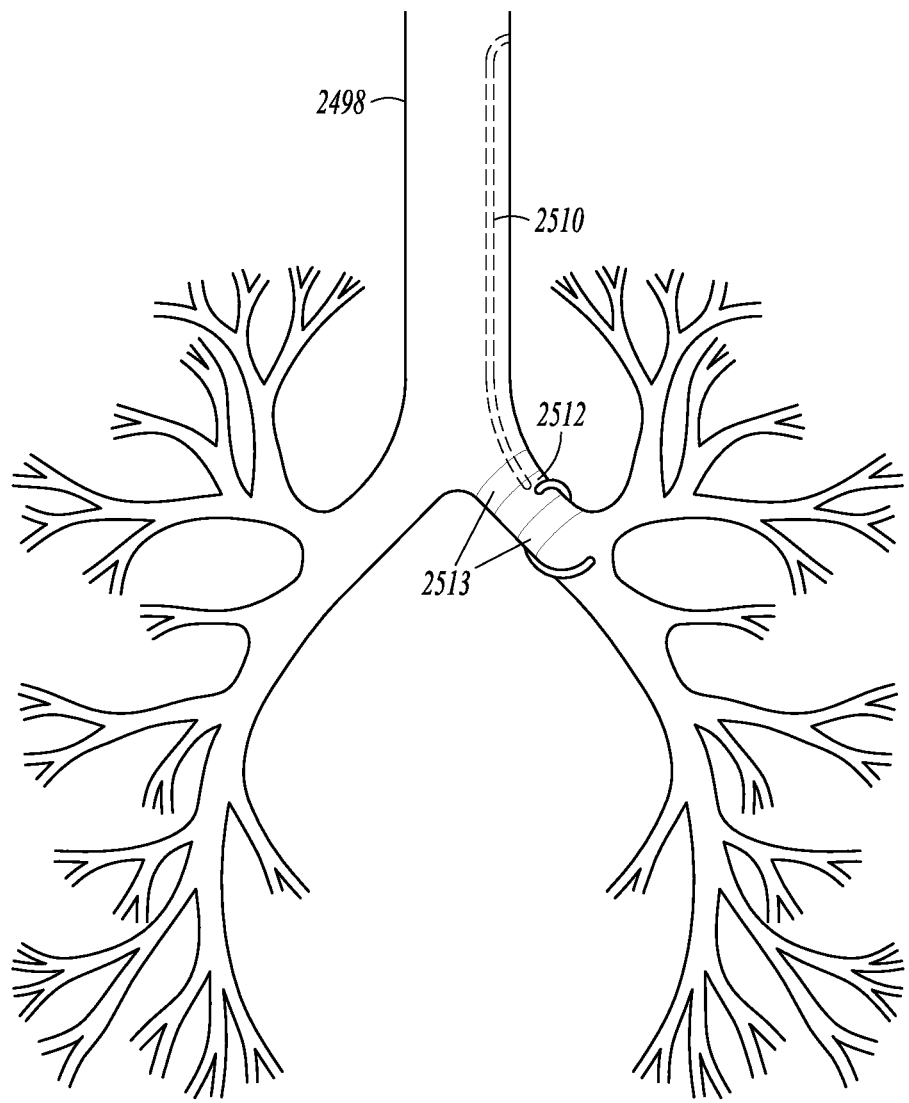
FIG. 25 illustrates an example of an embodiment in which a neurostimulation lead with electrodes is advanced through airways, puncturing through the airway wall at the location of electrode placement.

FIG. 25 illustrates an example of an embodiment in which a neurostimulation lead 2510 with electrodes is advanced through airways (e.g. trachea 2511/bronchi 2512), puncturing through the airway wall at the location of electrode placement. The distal end of the lead may be wrapped or otherwise positioned outside of the airway. For example, the lead may puncture through the airway wall between cartilage rings 2513. The lead may exit in the trachea and be tunneled to the location of the pacing device.

Figure 26:
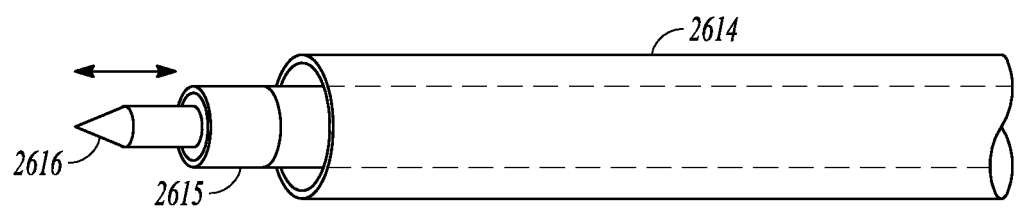
FIGS. 26-27 illustrate an example of an embodiment of a neurostimulation lead delivery system.
Figure 27:
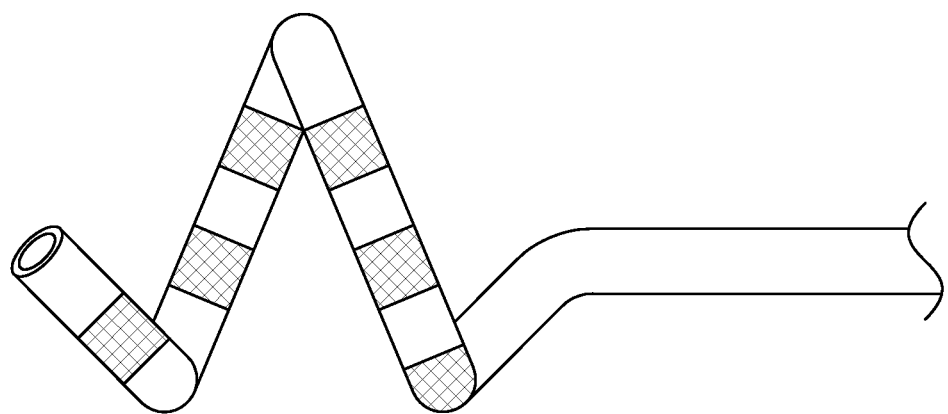

FIG. 26 illustrates an example of an embodiment of a neurostimulation lead delivery system. A lead delivery device 2614 such as steerable sheath or bronchoscope may be advanced through the airways to the desired location. The lead 2615 may be advanced through the lead delivery device 2614. The lead may include a puncturing needle 2616 for use to puncture through the airway at the desired location. The puncturing needle may be incorporated as part of the lead, or alternatively as a guidewire/puncturing member that is later removed from the lead. In some other embodiments the airway may be punctured using a laser or RF electrocautery insertion probe. The lead 2615 in a "free state" outside of the lead delivery device 2614 may be resemble the multipolar lead with a helical shape illustrated in FIG. 27.

Figure 28:
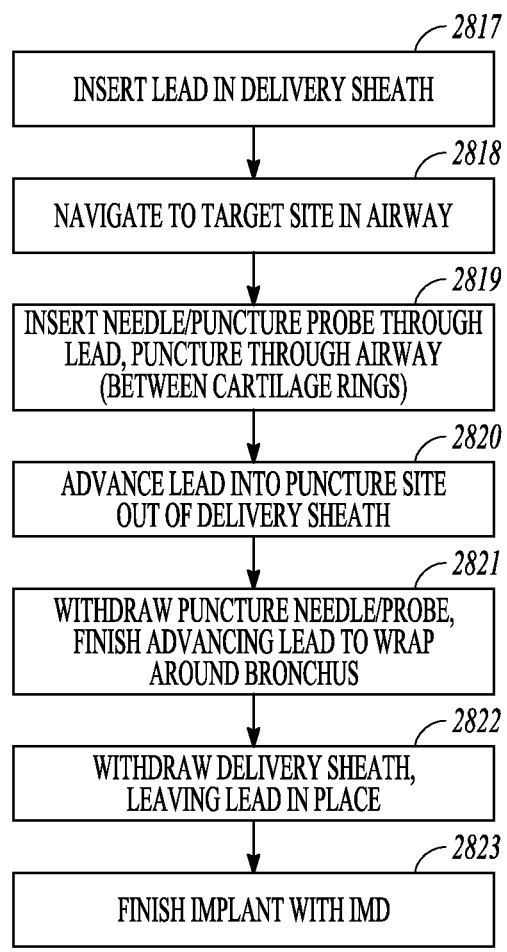
FIG. 28 illustrates, by way of example, a flow chart for implanting the lead illustrated in FIG. 24.

FIG. 28 illustrates, by way of example, a flow chart for implanting the lead illustrated in FIG. 24. At 2817 the lead may be inserted in a delivery sheath, and the sheath may be navigated to the target site in the airway at 2818. At 2819 a needle or puncture probe may be inserted through lead to puncture through the airway between cartilage rings. The lead may be advanced out of the delivery sheath and through the puncture site 2820. The puncture needle or probe may be withdrawn, and the lead may be wrapped around the bronchus 2821. The delivery sheath may be withdrawn leaving the lead in place 2822, and the implant may be completed by implanting the IMD 2823.

Cervical Vagus Nerve Stimulator

Some device embodiments include an implantable pulse generator that may be implanted in a similar manner as cardiac pacemakers, with at least one lead configured to deliver stimulation to the right vagus nerve, the left vagus nerve, or both the right and left vagus nerves. The electrode(s) on the lead may include a cuff electrode or a helical electrode. The lead may be configured to be intravascularly positioned proximate to the vagus nerve, such as in an Internal Jugular Vein (IJV). The lead may be multipolar lead configured to be implanted within the carotid sheath.

Figure 29:
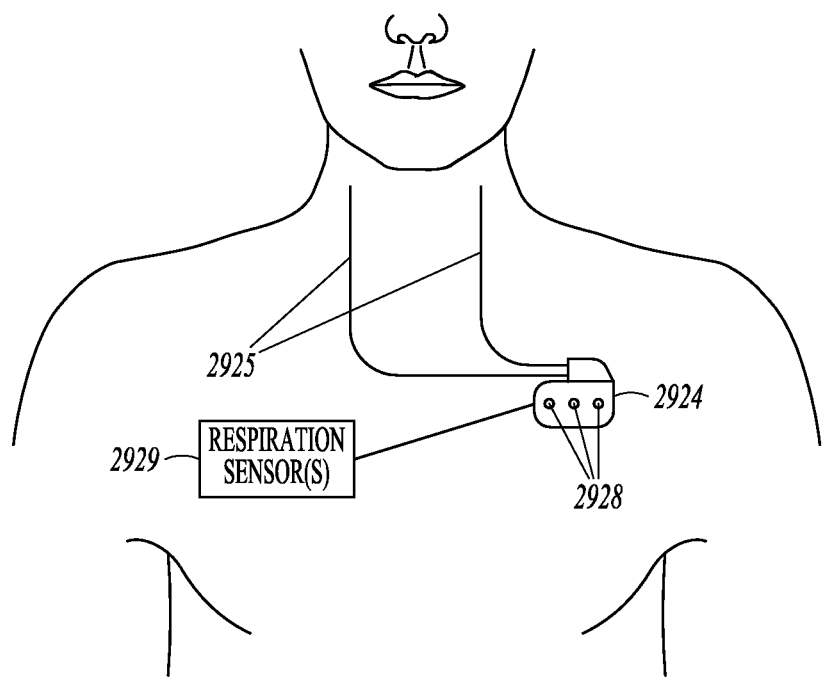
FIGS. 29-30 illustrate an example of system embodiments adapted to provide depletion block stimulation to a vagus nerve, and are illustrated as bilateral systems, by way of example and not limitation that may be used to provide stimulation to both the left and right vagus nerve.
Figure 30:
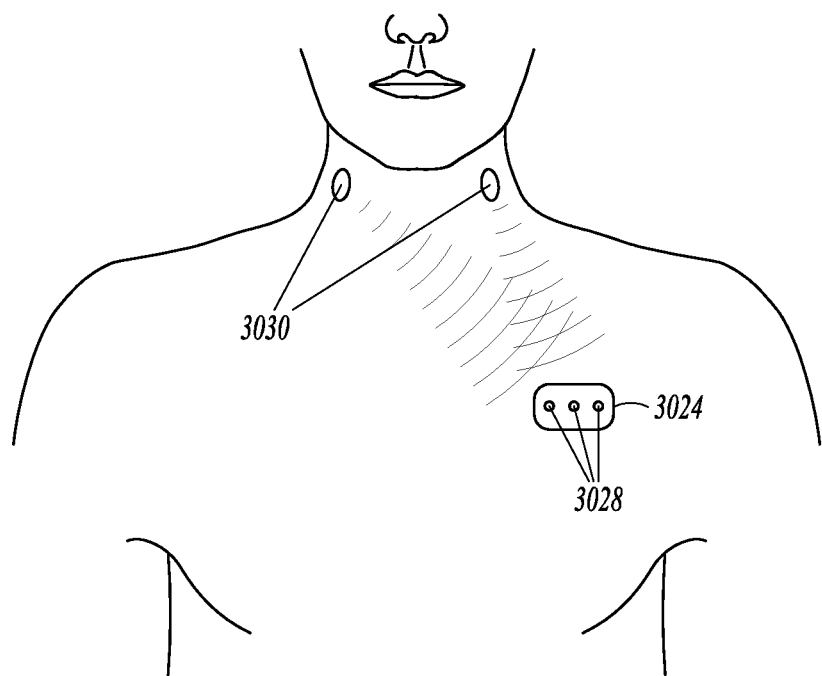

FIGS. 29-30 illustrate an example of system embodiments adapted to provide depletion block stimulation to a vagus nerve, and are illustrated as bilateral systems, by way of example and not limitation that may be used to provide stimulation to both the left and right vagus nerve. Those of ordinary skill in the art will understand, upon reading and comprehending this disclosure, that systems can be designed to stimulate only the right vagus nerve, systems can be designed to stimulate only the left vagus nerve, and systems can be designed to bilaterally stimulate both the right and left vagus nerves. The systems can be designed to stimulate nerve traffic (providing a parasympathetic response when the vagus is stimulated) as well as to provide depletion block.

FIG. 29 illustrates a system embodiment in which an IMD 2924 is placed subcutaneously or submuscularly in a patient's chest with lead(s) 2925 positioned to stimulate a vagus nerve. According to various embodiments, neural stimulation lead(s) 2925 may be subcutaneously tunneled to a neural target. Some embodiments may have a nerve cuff electrode or helical electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. Other embodiments deliver neural stimulation to the neural target from within the trachea, the laryngeal branches of the internal jugular vein, and the subclavian vein. The system may include leadless ECG electrodes 2926 on the housing of the device. These ECG electrodes are capable of being used to detect heart rate and detecting portions of the cardiac cycle, for example. The system may include respiration sensors(s) 2929, such as impedance or pressure sensors, that may be used to detect increased airway resistance.

FIG. 30 illustrates a system embodiment that includes an implantable medical device (IMD) 3024 with satellite electrode(s) 3030 positioned to stimulate at least one neural target. The satellite electrode(s) are connected to the IMD, which functions as the planet for the satellites, via a wireless link. Stimulation and communication can be performed through the wireless link. Examples of wireless links include RF links and ultrasound links. Examples of satellite electrodes include subcutaneous electrodes, nerve cuff electrodes and intravascular electrodes. Similar to the system of FIG. 29, the system of FIG. 30 may include leadless ECG electrodes on the housing of the device, and/or respiration sensors(s) 3029.

Figure 31:
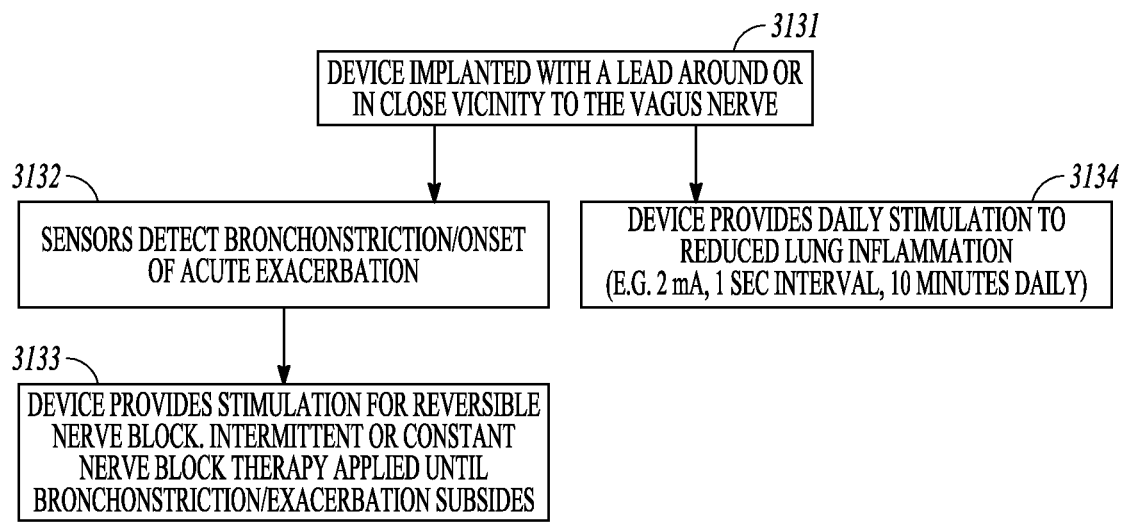
FIG. 31 illustrates an example of a flow chart for operating a vagal nerve stimulator configured to deliver a reversible depletion block.

FIG. 31 illustrates an example of a flow chart for operating a vagal nerve stimulator configured to deliver a reversible depletion block. At 3131, the device is implanted (e.g. a neurostimulation lead is implanted around or operably proximate to the vagus nerve). In some embodiments, sensor(s) maybe used to detect bronchoconstriction, mucus production or the onset of acute exacerbation (AECOPD) as illustrated at 3132. At 3133, the device may automatically deliver a reversible nerve block stimulation in response to the detected bronchoconstriction, mucus production/onset of acute exacerbation. The stimulation may be continuous or intermittent until the sensors indicate that the bronchoconstriction, mucus production/acute exacerbation has subsided. In some embodiments, as generally illustrated at 3134, the device may be programmed to provide continuous or intermittent stimulation to provide a depletion block to reduce bronchial tone and/or mucus production. Thus, the device may be used as a therapeutic response to a AECOPD, and may be used prophylactically to reduce bronchial tone and/or mucus production. The device may also be configured to respond to a command from the patient, a clinician, or other caregiver to initiate the nerve block to alleviate symptoms of AECOPD or to prophylactically lower bronchial tone and/or mucus production.

Some embodiments that provide a fiber-selective block of a nerve may set the stimulation parameters by finding the activation threshold (AT) and saturation threshold (ST) for size-driven thresholds to achieve fiber-selective block. The fiber-selective block may be implemented by setting the block between the ST for the smaller threshold fibers and the AT for larger threshold fibers. For example, if the smaller threshold fiber AT is 0.5 mA, the smaller threshold fiber ST is 0.9 mA, the larger threshold fiber AT is 3.0 mA, and the larger threshold fiber ST is 4.0 mA, then an smaller threshold fiber block may be delivered using 1 to 1.5 mA, a partial smaller threshold fiber block may be delivered using 0.6 mA, a complete smaller threshold fiber and partial larger fiber block may be delivered at 3.5 mA, and a complete smaller threshold fiber and larger threshold fiber block may be delivered at 4.5 mA.

Figure 32:
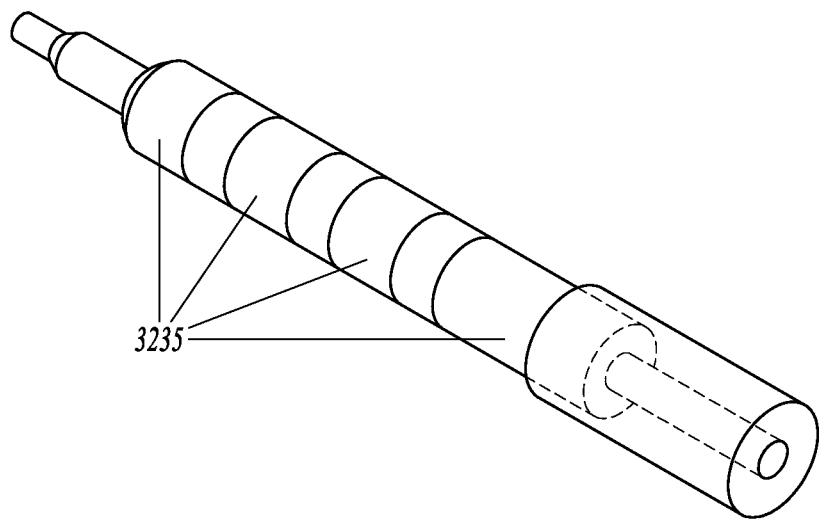
FIGS. 32-34 illustrate, by way of example and not limitation, some examples of leads that may be used to stimulate the vagus nerve.
Figure 33:
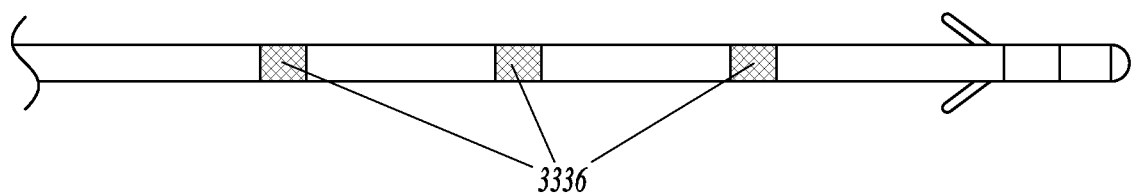
Figure 34:
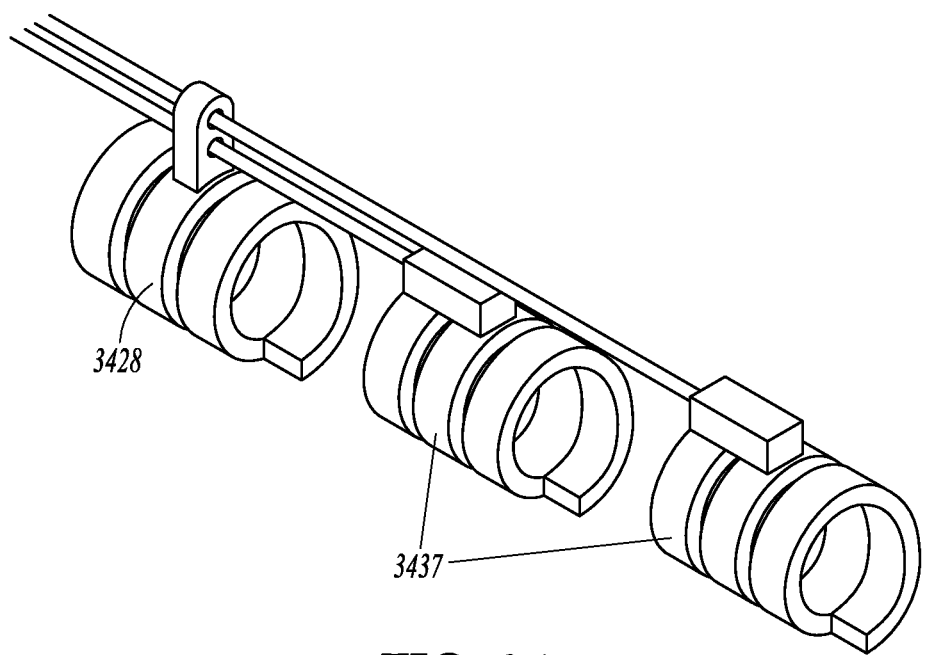

FIGS. 32-34 illustrate, by way of example and not limitation, some examples of leads that may be used to stimulate the vagus nerve. FIG. 32, for example, illustrates a multipolar terminal lead with more than one electrode 3235. FIG. 33, for example, illustrates a multipolar lead with low invasiveness and more than one electrode 3336. FIG. 34, for example, illustrates a lead with cuff electrodes 3437 and a strain-relief cuff 3438 for placement around a nerve trunk.

The above detailed description is intended to be illustrative, and not restrictive. The scope of the disclosure should, therefore, be determined with references to the appended claims, along with the full scope of equivalents to which such claims are entitled.

What is claimed is:

1. A system for delivering depletion block stimulation to a neural target that innervates airways using an implantable electrode near the neural target where the depletion block stimulation at a measurable activation threshold (AT) begins to increase nerve activity with increasing current amplitude and the depletion block stimulation at a measurable saturation threshold is where all or nearly all nerve fibers propagate action potentials such that nerve activity does not significantly increase in response to further increases in current amplitude, the system comprising:
the electrode which is configured to be implanted near the neural target that innervates airways; and
a pulse generation system configured to be operably connected to the electrode and programmed to deliver through the electrode a full depletion block stimulation where a current amplitude is at or above the saturation threshold followed by a partial depletion block where a stimulation intensity is reduced to a level below the saturation threshold and above the activation threshold to alleviate symptoms of pulmonary disease, the programmed pulse generation system and the electrode configured to cooperate to capture only some of the axons in the neural target when the partial depletion block is delivered to cause those captured axons to propagate action potentials and to capture all or almost all of the axons in the neural target when the full depletion block stimulation is delivered to cause those captured axons to propagate action potentials wherein both the full depletion block stimulation and the partial depletion block stimulation include a series of pulses within a depletion frequency range between about 100 Hz to about 1 kHz such that the series of pulses generate action potentials in the captured axons but block communication across synaptic clefts.

2. The system of claim 1, further comprising an electrode device, the electrode device including the electrode and configured to be implanted in an airway operably proximate to the neural target.

3. The system of claim 2, wherein the pulse generation system includes a pulse generator, a controller and a power supply configured to cooperate to deliver the depletion block stimulation through the electrode.

4. The system of claim 1, wherein the electrode includes an expandable structure configured to be expanded within the airway to contact an interior surface of the airway structure, the expandable structure including a pacing surface, the pacing surface including:
a smooth surface configured to abut against an interior surface of a wall for the airway structure; or
a surface with protrusions configured penetrate partially into or fully through the wall for the airway structure; or
a surface with a non-penetrating surface texture.

5. The system of claim 1, further comprising a stimulation lead, the lead including the electrode, the lead configured to be implanted to position the electrode external to an airway proximate to the neural target.

6. The system of claim 5, wherein the stimulation lead is configured to wrap at least partially around the airway to position the electrode proximate to the neural target.

7. The system of claim 5, wherein the stimulation lead is configured to be advanced within the airway, configured with an end to puncture a wall of the airway, and configured to wrap at least partially around the airway to position the electrode proximate to the neural target.

8. The system of claim 1, wherein the electrode is configured to be implanted operably proximate to:
a first generation bronchi for use in stimulating a pulmonary nerve branch that traverses along the first generation bronchi; or
a second generation bronchi for use in stimulating a pulmonary nerve branch that traverses along the second generation bronchi; or
a third generation bronchi for use in stimulating a pulmonary nerve branch that traverses along the third generation bronchi.

9. The system of claim 1, wherein the electrode is configured to be implanted near a cervical vagus nerve.

10. The system of claim 1, further comprising at least one sensor configured to sense a parameter correlated to increased airway resistance, the pulse generation system operably connected to the at least one sensor to detect an increase in airway resistance and configured to automatically initiate delivery of the depletion block stimulation in response to the detected increase in airway resistance.

11. The system of claim 10, wherein the sensor includes an impedance sensor configured to sense a reduction in transthoracic impedance.

12. The system of claim 10, wherein the sensor includes a pressure sensor configured to sense a reduction in pleural pressure.

13. The system of claim 1, wherein the pulse generation system is configured to receive a human-initiated command, and is configured to automatically initiate delivery of the depletion block stimulation in response to the received command.

* * * * *